US010416131B2

(12) United States Patent
Verenchikov

(10) Patent No.: US 10,416,131 B2
(45) Date of Patent: Sep. 17, 2019

(54) GC-TOF MS WITH IMPROVED DETECTION LIMIT

(71) Applicant: LECO Corporation, St. Joseph, MI (US)

(72) Inventor: Anatoly N. Verenchikov, St. Petersburg (RU)

(73) Assignee: LECO Corporation, St. Joseph, MI (US)

( * ) Notice: Subject to any disclaimer, the term of this patent is extended or adjusted under 35 U.S.C. 154(b) by 322 days.

(21) Appl. No.: 15/300,720

(22) PCT Filed: Mar. 31, 2015

(86) PCT No.: PCT/US2015/023640
§ 371 (c)(1),
(2) Date: Sep. 29, 2016

(87) PCT Pub. No.: WO2015/153644
PCT Pub. Date: Oct. 8, 2015

(65) Prior Publication Data
US 2017/0168031 A1    Jun. 15, 2017

Related U.S. Application Data

(60) Provisional application No. 61/973,090, filed on Mar. 31, 2014.

(51) Int. Cl.
*G01N 30/72* (2006.01)
*H01J 49/40* (2006.01)
(Continued)

(52) U.S. Cl.
CPC ........ *G01N 30/7206* (2013.01); *H01J 49/004* (2013.01); *H01J 49/0031* (2013.01);
(Continued)

(58) Field of Classification Search
CPC ........................ G01N 30/7206; H01J 49/0031; H01J 49/004; H01J 49/061; H01J 49/067; H01J 49/10; H01J 49/147; H01J 49/406
(Continued)

(56) References Cited

U.S. PATENT DOCUMENTS 6,888,130 B1 *   5/2005  Gonin .................... H01J 9/027
                                                        250/281
7,838,824 B2    11/2010  Vestal
(Continued)

FOREIGN PATENT DOCUMENTS

JP    2008535164 A    8/2008
JP    2013525986 A    6/2013
(Continued)

OTHER PUBLICATIONS

International Search Report dated Jun. 22, 2015, relating to International Application No. PCT/2015/023640.
(Continued)

*Primary Examiner* — Nicole M Ippolito
(74) *Attorney, Agent, or Firm* — Honigman LLP

(57) ABSTRACT

For improving sensitivity, dynamic range, and specificity of GC-MS analysis there are disclosed embodiments of novel apparatuses based on improved characteristics of semi-open source with electron impact ionization, providing much higher brightness compared to known open EI sources. In an implementation, the source becomes compatible with multi-reflecting TOF analyzers for higher resolution analysis for improving detection limit. With improved schemes of spatial and temporal refocusing there are proposed various tandem TOF-TOF spectrometers with PSD, CID, and SID fragmentation and using either singly reflecting TOF or MR-TOF analyzers.

10 Claims, 13 Drawing Sheets

(51) Int. Cl.
*H01J 49/06* (2006.01)
*H01J 9/00* (2006.01)
*H01J 49/10* (2006.01)
*H01J 49/00* (2006.01)
*H01J 49/14* (2006.01)

(52) U.S. Cl.
CPC .......... *H01J 49/061* (2013.01); *H01J 49/067* (2013.01); *H01J 49/10* (2013.01); *H01J 49/147* (2013.01); *H01J 49/406* (2013.01)

(58) Field of Classification Search
USPC ................ 250/281, 282, 283, 286, 287, 288
See application file for complete search history.

(56) References Cited

U.S. PATENT DOCUMENTS

| | | |
|---|---|---|
| 2008/0111070 A1 | 5/2008 | Makarov et al. |
| 2012/0091330 A1* | 4/2012 | Coon ................ H01J 9/004 250/282 |
| 2013/0056627 A1* | 3/2013 | Verenchikov ........ H01J 9/406 250/282 |
| 2013/0068942 A1* | 3/2013 | Verenchikov ....... H01J 49/4245 250/282 |

FOREIGN PATENT DOCUMENTS

| | | |
|---|---|---|
| JP | 2013539590 A | 10/2013 |
| WO | WO-2013110588 A2 | 8/2013 |
| WO | WO-2013163530 A2 | 10/2013 |
| WO | WO-2013192161 A2 | 12/2013 |

OTHER PUBLICATIONS

Japanese Office Action for the related Application No. 2016-560414 dated Jul. 13, 2018.

* cited by examiner

GC-TOF MS WITH IMPROVED DETECTION LIMIT

CROSS-REFERENCE TO RELATED APPLICATIONS

This application claims priority under 35 U.S.C. § 371 to Patent Cooperation Treaty Application No. PCT/US2015/023640, filed Mar. 31, 2015, which claims priority under 35 U.S.C. § 119(e) to U.S. Provisional Application No. 61/973,090, filed Mar. 31, 2014. The disclosures of these prior applications are considered part of the disclosure of this application and are hereby incorporated by reference in their entireties.

TECHNICAL FIELD

This disclosure generally relates to mass spectroscopic analysis and more specifically to improving the sensitivity of time-of-flight mass spectrometers with gas chromatograph and an electron impact ion source and with providing MS-MS features in such instrument.

BACKGROUND

Chromato-mass spectrometers GC-MS, is a combination of a gas chromatograph (GC), an electron impact ionization source (EI), and a mass spectrometer (MS). GC-MS are widely used for environmental, forensic, and clinical applications. Whenever analyte compounds are volatile enough, GC-MS is preferred over LC-MS, since it provides high-resolution and highly predictive chromatography, quantitative ionization, and NIST library identification.

GC-MS can be used in a number of applications, such as analyses as PCB and pesticides that require analyses in wide dynamic range over 6 or 7 orders of magnitude. The upper load into the GC column is limited to approximately 10 ng (1E-8 g) per compound both by the gas chromatography (at 1 mL/min helium flow) and by the linear response of EI sources. Thus, a desire for a large dynamic range translates into improving the detection limit (LOD) to a level around 1-10 fg (1E-15 g-1E-14 g) per trace compound of interest within complex matrices.

Most common GC-MS instruments employ quadrupole analyzers due to their low cost. Though these instruments employ so-called "closed" EI sources, which concentrate sample and improve ionization efficiency to approximately 1%, the LOD of quadrupolar GC-MS only reaches approximately 1 pg (1E-12 g), primarily due to mass scanning losses in the quadrupolar analyzers and to low resolution of the mass analyzer.

GC-TOF (such as the Pegasus GC-TOF by LECO Corp, Michigan, US) provides several analytical advantages over quadrupole GC-MS. A singly reflecting time-of-flight (TOF MS) analyzer provides rapid spectral acquisition and detects all ions in a full mass range without scanning losses. The analyzer has wide spatial acceptance, which is sufficient for unity ion transmission. Because of fast and non-skewed spectral acquisition, GC-TOF allows fast GC and better de-convolution of partially overlapping GC peaks, such as multi-dimensional GC (GC×GC) for enhanced separation of up to about 10,000 components.

While quadrupolar GC-MS employ so-called "closed" EI sources, generating a continuous ion beam, GC-TOF employ so-called "open" EI sources, accumulating ions within a potential well of an electron beam, which eliminates ion losses between pulses of the TOF analyzer. An "open" electron impact (EI) ion source has earned the reputation of a robust and never-cleaned EI source. GC-TOF provides strong ionic signals—up to 10,000 ions per pulse at 10 kHz frequency. However, the detection limit (LOD) has been comparable to quadupole GC-MS (i.e. 1 pg).

Compared to "open" sources, the LOD of GC-TOF has been improved to about 100 fg with the introduction of semi-open EI ion sources (so-EI) per WO2013163530, which improves sample ionization efficiency and concentrates analyte molecules (but not the chemical background), while still preserving ion accumulation features. The LOD also improves to100 fg when using standard "open" EI source and dual stage GC×GC because of temporal sample concentration over the chemical background and matrix. Both observations indicate that LOD may be limited primarily by mass spectral interference with a complex matrix and chemical background (say, oil from pumping system). Then, one would expect better LOD when using instruments of higher specificity, either of higher resolution at single MS or of higher selectivity at tandem MS-MS.

Recently introduced GC-MR-TOF (such as "Citius GC-HRT" by LECO Corp) employs a closed EI source and high resolution multi-reflecting TOF (MR-TOF) analyzers with orthogonal accelerator (OA). In spite of high resolution (R=25-40K) the instrument also has comparable LOD=0.1-1 pg, most likely because of duty cycle losses in the OA at rare MR-TOF pulses.

Recently emerging GC-Q-TOF tandems (such as the GC-Q-TOF by Agilent) employ a "closed" EI source, quadrupole filter for selecting parent ions, CID cell for ion fragmentation, and singly reflecting TOF with an orthogonal accelerator for fragment analysis. In spite of improved specificity (MS-MS is expected to separate analyte signal from matrix and chemical background), GC-Q-TOF has demonstrated a LOD of only about 0.1 pg (i.e. a moderate improvement compared to previous GC-MS), presumably due to ion losses in transfer optics and duty cycle losses in the orthogonal accelerator.

Thus, existing GC-MS instrumentation have not improved LOD to a 1-10 fg level by using multiple means including: highly efficient "closed" EI sources; accumulating open and semi-open EI sources; non-scanning TOF analyzer with wide acceptance; high resolution MR-TOF instruments; and highly selective MS-MS instruments.

Thus, there still remains a practical problem of improving sensitivity at GC-MS analysis, preferably implemented in low complexity instruments while using robust and fast responding EI source and also having soft ionization features.

SUMMARY

The inventors realized that sensitivity of wide-spread GC-TOF instruments (with open EI sources and with singly reflecting TOF analyzers) is primarily limited by mass spectral interferences with the matrix and chemical background, rather than by efficiency of ionization or analyzer transmission. Thus, to improve LOD, enhancement of either resolution of analyzers or specificity of analysis with tandem MS-MS features, while preserving high ion transmission, is needed in the art.

Inventors also realized that a semi-open electron impact ion source (so-EI), proposed by inventors in WO2013163530, improves both ionization efficiency and analyte per background ratio. In presently disclosed invention-related studies of so-EI source inventors further discovered that the so-EI source provides much higher brightness (i.e. ratio of signal to ion packet phase space) compared to an open source, earlier used for TOF MS.

Novel methods of effective coupling between the so-EI source and high resolution multi-reflecting Time-of-flight (MR-TOF) analyzers which provide for high ion transmission, low time-of-flight aberrations, and large dynamic range are disclosed. Further novel methods of coupling of so-EI source with low gas pressure CID and various SID fragmentation cells, which provide for high ion transmission, low time-of-flight aberrations and large dynamic range, thus making so-EI-MR-TOF suitable for various tandem TOF techniques, are also disclosed. Those apparatuses and methods are expected to improve specificity of the analysis (i.e. differentiation between sample, matrix, and chemical background), and, accordingly, to improve the sensitivity and reliability of the analysis.

The inventors further realized that sensitivity of so-EI-MR-TOF may be also improved by operating the closed EI source at frequent and soft pulsed ion ejection mode, followed by pulsed "bunching" (i.e. pulsed acceleration for compressing ion packets time spread). Yet further improvement of GC-MS LOD is disclosed by suppressing chemical background in several simple ways.

According to the first aspect of the disclosure, a chromato-mass spectrometer includes a single or dual stage gas chromatograph, a semi-open nEI source, a multi-reflecting time-of-flight analyzer, and an interface. The semi-open EI source has a source opening between about 0.1 to 1 $cm^2$ and has positively biased slits for electron beam. The semi-open EI source is arranged in a separate differential pumping stage, provides ion storage in an electron beam, and provides pulsed ejection of accumulated ions. The multi-reflecting time-of-flight analyzer includes a periodic lens and a time-of-flight detector. The interface includes a set of focusing and deflecting ion-optical elements coupling the ion source with the analyzer such that the spatial emittance of the ion source is matched to the acceptance of the analyzer and that time broadening of the ion signal due to the spatial emittance is eliminated at the detector at least to the first order of the Tailor expansion.

Preferably, to increase the dynamic range by frequent encoding pulsing, the apparatus may further comprise: (i) a synchronizing clock with capability of triggering at programmed non uniform time interval with time increments no more than about 10 ns; (ii) a pulse generator configured to pulse at an average frequency at least about 30 kHz; and (iii) a data system for spectral decoding. Preferably the detector includes a magnetic ion-to-electron converter, a scintillator covered by conductive mesh, and a photo-electron multiplier with extended life time. Those features may aid in handling large ion fluxes, expected in 1E+9 ion/sec range.

In an implementation, the interface may be selected from the group consisting of (i) a differentially pumped chamber, accommodating said ion source and placed between said ion mirrors; (ii) an isochronous set of curved electrostatic sectors for external mounting of said source; (iii) an isochronous set of curved electrostatic sectors for displacing ion trajectory; (iv) an energy filter composed either of electrostatic sectors or deflectors combined with spatially focusing lens; (v) a lens-deflector with pulsed power supply for deflecting helium ions or for crude mass selection; (vi) a gridless ion mirror placed behind said ion source; (vii) a curved field accelerator built into said source for isochronous spatial focusing; (viii) a differential aperture placed at a plane of spatial focusing and followed by spatially focusing lens; (ix) a telescopic lens system for reducing spatial packet size at the expense of widening angular spread; and (x) a combination thereof. Those embodiments help for practical coupling of wide and diverging packets past so-EI source to MR-TOF analyzer with limited phase space acceptance and with difficult ion injection from spatially wide sources.

In an implementation, preferably, parameters of the MR-TOF analyzer are characterized by at least one of: (i) a cap to-cap distance between about 0.5 m and 1.5 m; (ii) a periodic lens with lens pitch between about 5 mm and 20 mm; (iii) an ion flight path between about 7 m and 30 m; and (iv) an acceleration voltage between about 3 keV and 10 keV. Preferably, said MR-TOF analyzer is of either planar or cylindrical symmetry. Such parameters are chosen to provide at least about 20-25K resolution in order to separate semi-volatile compounds with nitrogen and oxygen content from ubiquitous hydrocarbons.

In an implementation, the apparatus may further include an ion transferring optics for introducing external ions into the so-EI source and one source selected from the group consisting of: (i) a chemical Ionization source; (ii) a photo chemical ionization source; and (iii) an ion source with conditioned plasma. In an implementation, preferable, said apparatus may further comprise an inlet for external delivery of analyte molecules selected from the group consisting of: (i) molecular beam generator; (ii) molecular separator for splitting helium and analyte flows. Those embodiments, extend GC-MS capabilities for softer ionization and wider range of gas chromatographic fluxes while using similar or the same differential pumping setup at sample introduction.

In an implementation, preferably, for the purpose of providing MS-MS capabilities, the apparatus further includes at least one means selected from the group consisting of: (i) a timed ion selector for selecting parent ions past said ion source; (ii) a gridless ion mirror behind said so-EI source for simultaneous temporal and spatial focusing of primary ions into a fragmentation cell; (iii) a curved-field accelerator built into said so-EI source for simultaneous temporal and spatial focusing of primary ions into a fragmentation cell; (iv) a surface induced dissociation SID cell facing primary ion packets; (v) a surface induced dissociation SID arranged at gliding angle relative to trajectory of parent ion packets; (vi) a collisional induced dissociation CID within a short CID cell with length L under about 1 cm at gas pressure P adjusted for P*L product at or between about 1 and 5 cm*mTor corresponding to single average collision of parent ions; (vii) a collisional induced dissociation CID cell arranged within said source by choosing said source opening between about 0.1 and 0.3 $cm^2$; (viii) pulsed accelerator past a fragmentation cell; (ix) spatial focusing lens past a fragmentation cell; (x) post-acceleration of fragment ion packets past a fragmentation cell; (xi) steering means past a fragmentation cell; and (xii) a combination thereof. Preferably, the apparatus further comprises a pulse generator past said source for one purpose of the group: (i) adjusting time focal plane of ion packets, pulse ejected from said source; (ii) adjusting energy or energy spread of ion packets, pulse ejected from said source; (iii) converting a continuous flow past said source into ion packets, followed by energy filtering of said ion packets.

According to the second aspect of the disclosure, a method of chromato-mass spectrometric analysis includes:
separating analyte mixture by single or dual stage gas chromatography; injecting analyte molecules into an ionization chamber having opening between about 0.1 to 1 $cm^2$ for improving ratio between analyte molecules Vs chemical background;

ionizing analyte molecules by electron beam passing slits, said slits being positively biased relative to electrodes surrounding ionization volume for retaining analyte ions and for removing secondary electrons; pulsed ejecting ion packets;

refocusing of said ion packets spatially and temporally to match emittance of the following mass spectral analysis;

adjusting spatial spread and filtering energy spread of said ion packets to match acceptance of the following mass spectral analysis;

adjusting time front inclinations of said ion packets to reach minimal time spread of ion signal at ion detector;

pulsed or continuous steering of ion packets for alignment;

separating ion packets in time at isochronous multiple reflections between electric fields of gridless ion mirrors, separated by a field free region, and spatially confining said ion packets in the drift direction by periodic focusing lens placed in said field-free region;

detecting said ion packets with a time-of-flight detector to form waveform signal; and analyzing said signal to extract mass spectra and chromato-mass spectral information.

In an implementation, preferably, for the purpose of increasing the dynamic range of said analysis, said step of ion ejection is arranged at periods at least about 10 times smaller compared to ion flight time at said time separation step; encoding ejecting pulses with mostly unique time intervals between adjacent pulses at time increments no less than ion packet time width; and decoding partially overlapped signals corresponding to multiple ejection pulses at said spectral analysis step.

In an implementation, preferably, said steps of ion refocusing and alignment ion packets past said ion ionization step may comprise at least one step of the group: (i) accommodating said ionization chamber between said ion mirrors and differentially pumping a housing surrounding said chamber in order to minimize ion packet steering; (ii) accommodating said ionization chamber externally to said ion mirrors and transferring ion packets through electric fields of an isochronous set of curved electrostatic sector; (iii) displacing ion trajectory with electric fields of an isochronous set of curved electrostatic sectors; (iv) energy filtering of ion packets either within electrostatic sectors or by spatially focusing and deflecting said ion packets; (v) pulsed deflecting helium ions or ions under some preset mass threshold; (vi) isochronous spatial focusing of ion packet by gridless ion mirror placed behind said ionization chamber; (vii) pulse accelerating ion packets with isochronous curved field arranged within and past said ionization chamber; (viii) spatially focusing of ion packets into a differential aperture followed by spatially focusing past said aperture to form substantially parallel ion trajectories; (ix) a telescopic focusing of said ion packets for reducing spatial packet size at the expense of widening the ion packet angular spread; and (x) a combination thereof.

In an implementation, preferably, said step of ion time separation is selected from the group consisting of: (i) arranging the ion mirrors with cap to-cap distance between about 0.4 m and 1.5 m; (ii) arranging said periodic spatial focusing in the drift direction with period between about 5 mm and 20 mm; (iii) arranging ion flight path between about 7 m and 30 m; (iv) accelerating injected ion packets by voltage between about 3 keV and 10 keV; preferably, said electric field of ion mirrors is of either planar or cylindrical symmetry; and (v) a combination thereof.

Preferably, the method may further comprise the following steps: forming analyte ions externally to said ionization chamber, transferring continuous ion beam of externally formed ions into said ionization chamber at ion energy between about 5 eV and 100 eV, pulse accelerating a portion of said continuous ion beam into a time-of-flight separator, and steering thus formed ion packets to align their trajectory for time-of-flight separating step; and wherein said external ionization method is selected from the group consisting of: (i) chemical Ionization; (ii) photo chemical ionization; and (iii) ionization with conditioned plasma. Preferably, said step of ion injection into said ionization chamber may be selected from the group consisting of: (i) forming a directed molecular beam of vibrationally cold analyte molecules within a differential pumping system with collimation of a supersonic gas jet; (ii) splitting a portion of analyte molecular flow and of chromatographic gas flow within a differentially pumped system; and (iii) a combination thereof.

Preferably, said detection step may comprise the following steps: ion to electron converter at surface parallel to ion packet time-front; accelerating electrons by potential difference between said conversion surface and said field-free region; magnetic steering secondary electrons between about 30 degrees and 180 degrees; accelerating said secondary electrons to a scintillator covered by conductive mesh for removing electrostatic charging, thus producing multiple photons per single electron; and detecting said photons with photo-electron multiplier.

Preferably, for the purpose of providing MS-MS capabilities, the method may further be selected from the group consisting of: (i) a timed ion selection of parent ions past said ionization step; (ii) ejecting ions at reverse direction into electrostatic field of a gridless ion mirror placed behind said ionization chamber and simultaneous temporal and spatial focusing of primary ion packets into a fragmentation cell formed inside said ionization chamber or placed past said ionization chamber; (iii) simultaneous temporal and spatial focusing of primary ions into a fragmentation cell within a curved field of accelerator within said ionization chamber and past said ionization chamber; (iv) fragmenting ion packets at collision with a surface placed parallel to time-front of said ion packets followed by a delayed pulsed extraction of thus formed fragment ions; (v) fragmenting ion packets at collision with a surface arranged at gliding angle relative to parent ion trajectory followed by a static or pulsed acceleration of thus formed fragment ions; (vi) a collisional induced dissociation arranged within a cell with length L under about 1 cm at gas pressure P adjusted for P*L product between about 1 cm*mTor and 5 cm*mTor corresponding to single average collision of parent ions; (vii) a collisional induced dissociation arranged within said ionization chamber by choosing said chamber opening between about 0.1 and 0.3 $cm^2$ at 1 ml/min gas flow from said chromatograph; (viii) pulsed acceleration past a fragmentation step; (ix) spatial focusing past a fragmentation step; (x) post-acceleration of fragment ion packets past a fragmentation step; (xi) steering past a fragmentation step; and (xii) a combination thereof.

Preferably, the method may further comprise a step of pulsed acceleration of ion packets for one purpose of the group: (i) adjusting time focal plane of ion packets past said step of ion ejection; (ii) adjusting energy or energy spread of ion packets past said step of ion ejection; (iii) converting a continuous or a quasi-continuous flow past said ionization chamber, followed by a step of energy filtering of said pulsed accelerated ion packets; and (iv) a combination thereof. Preferably, said step of ion packet refocusing may comprise a step of converting wide (about 7-10 mm) and low divergent ion packets (<5-6 mrad) into smaller size (about 3-5 mm) and wider diverging (about 15-20 mrad) packets with conversion factor between about 2 and 5.

Preferably, for the purpose of improving dynamic range of said analysis, the method may further comprise a step of alternating ion packet intensity (gain) between ion ejections and recording separate data sets corresponding to different gains and wherein said intensity alternation method comprises one the group: (i) alternating the duration of push out pulse to vary the duration of electron beam ionization; (ii) alternating the spatial focusing of ion packets at any stage with a preference to earlier stages of ion transfer; (iii) alternating the detector gain; (iv) alternating ion path between wide open and smaller area apertures; and (v) a combination thereof.

Preferably, the method may further comprising a step of improving ratio of analyte molecules to chemical background of pumping system by one step of the group: (i) enclosing or coating with electro-less nickel of porous magnets employed at electron ionization step; (ii) introducing an additional gas flow past turbo-pumping of the source housing to avoid diffusion of oil from mechanical pump; (iii) choosing small size between about 0.5 L/s to 1 L/s mechanical pump to sustain sufficiently viscous flow in the mechanical pumping line, thus preventing oil diffusion; and (iv) a combination thereof.

According to a third aspect of the disclosure, a mass spectrometer includes a semi-open EI source, a time-of-flight analyzer, a fragmentation cell, and a means for enhancing the MS-MS capabilities of the spectrometer. The semi-open EI source defines a source opening between 0.1 and 1 square centimeter and is adapted to provide pulsed ejection of accumulated ions. The time-of-flight analyzer has a time-of-flight detector. The fragmentation cell is incorporated into the TOF analyzer for MS-MS capabilities. The means for enhancing said MS-MS capabilities of the spectrometer is selected from the group consisting of: (i) a timed ion selector for selecting parent ions past said ion source; (ii) a gridless ion mirror behind said so-EI source for simultaneous temporal and spatial focusing of primary ions into a fragmentation cell; (iii) a curved-field accelerator built into said so-EI source for simultaneous temporal and spatial focusing of primary ions into a fragmentation cell; (iv) a surface induced dissociation SID cell facing primary ion packets; (v) a surface induced dissociation SID arranged at gliding angle relative to trajectory of parent ion packets; (vi) a collisional induced dissociation CID within a short CID cell with length L under 1 cm at gas pressure P adjusted for P*L product between 1 and 5 cm*mTor corresponding to single average collision of parent ions; (vii) a collisional induced dissociation CID cell arranged within said source by choosing said source opening between 0.1 and 0.3 cm$^2$; (viii) pulsed accelerator past a fragmentation cell; (ix) spatial focusing lens past a fragmentation cell; and (x) post-acceleration of fragment ion packets past a fragmentation cell; (xi) steering means past a fragmentation cell; and (xii) a combination thereof.

Implementations of this aspect of the disclosure may include one or more of the following features. In some implementations, the TOF analyzer is one of the group: (i) linear TOF; (ii) singly reflecting TOF; (iii) TOF containing at least one electrostatic sector; (iv) multi-reflecting TOF analyzer. In some examples, the mass spectrometer further includes a pulse generator past the so-EI source for a purpose selected from the group consisting of: (i) adjusting time focal plane of ion packets, pulse ejected from said source; (ii) adjusting energy or energy spread of ion packets, pulse ejected from said source; (iii) converting a continuous flow past said source into ion packets, followed by energy filtering of said ion packets; and (iv) combination thereof. Optionally, to increase dynamic range by frequent encoding pulsing, the mass spectrometer further includes a synchronizing clock, a pulse generator, and a data system for spectral decoding. The synchronizing clock has capabilities for triggering at programmed non-uniform time intervals with time increments no more than 10 ns; (ii) pulse generator with capability for pulsing at average frequency at least 30 kHz; and (iii) a data system for spectral decoding.

In some implementations, the mass spectrometer further includes an interface selected from the group consisting of: (i) a differentially pumped chamber, accommodating said ion source and placed between said ion mirrors; (ii) an isochronous set of curved electrostatic sectors for external mounting of said source; (iii) an isochronous set of curved electrostatic sectors for displacing ion trajectory; (iv) an energy filter composed either of electrostatic sectors or deflectors combined with spatially focusing lens; (v) a lens-deflector with pulsed power supply for deflecting helium ions or for crude mass selection; (vi) a gridless ion mirror placed behind said ion source; (vii) a curved field accelerator built into said source for isochronous spatial focusing; (viii) a differential aperture placed at a plane of spatial focusing and followed by spatially focusing lens; (ix) a telescopic lens system for reducing spatial packet size at the expense of widening angular spread; and (x) a combination thereof. In some examples, parameters of the MR-TOF analyzer are selected from the group consisting of: (i) a cap to-cap distance between 0.5 m and 1.5 m; (ii) a periodic lens with lens pitch between 5 mm and 20 mm; (iii) an ion flight path between 7 and 30 m; (iv) an acceleration voltage between 3 keV and 10 keV; and (v) a combination thereof. Optionally, the MR-TOF analyzer is of either planar or cylindrical symmetry.

In some implementations, the mass spectrometer further includes ion transferring optics for introducing external ions into the so-EI source and one source selected from the group consisting of: (i) a chemical ionization source; (ii) a photo chemical ionization source; and (iii) an ion source with conditioned plasma. Optionally, the mass spectrometer further includes an inlet for external delivery of analyte molecules from one source selected from the group consisting of (i) a molecular beam generator; (ii) a molecular separator for splitting helium and analyte flows; and (iii) a combination thereof. In some examples, the detector includes a magnetic ion to electron converter, a scintillator covered by conductive mesh, and photo-electron multiplier with extended life time.

According to a fourth aspect of the disclosure, a method of chromato-mass spectrometric analysis includes the following steps: ionizing analyte molecules by electron beam passing slits of an ionization chamber, said slits being positively biased relative to electrodes surrounding ionization volume for retaining analyte ions and for removing secondary electrons; pulse ejecting ion packets; ion separation in a time-of-flight analyzer; ion fragmentation for MS-MS analysis; and at least one step of enhancing the MS-MS selected from the group consisting of: (i) a timed ion selection of parent ions after said ionization step; (ii) ejecting ions at reverse direction into electrostatic field of a gridless ion mirror placed behind said ionization chamber and simultaneous temporal and spatial focusing of primary ion packets into a fragmentation cell formed inside said ionization chamber or placed past said ionization chamber;

(iii) simultaneous temporal and spatial focusing of primary ions into a fragmentation cell within a curved field of accelerator within said ionization chamber and past said ionization chamber; (iv) fragmenting ion packets at collision with a surface placed parallel to time-front of said ion packets followed by a delayed pulsed extraction of thus formed fragment ions; (v) fragmenting ion packets at collision with a surface arranged at gliding angle relative to parent ion trajectory followed by a static or pulsed acceleration of thus formed fragment ions; (vi) a collisional induced dissociation arranged within a cell with length L under 1 cm at gas pressure P adjusted for P*L product between 1 and 5 cm*mTor corresponding to single average collision of parent ions; (vii) a collisional induced dissociation arranged within said ionization chamber by choosing said ionization chamber opening between 0.1 and 0.3 cm² at 1 ml/min gas flow from a chromatograph; (viii) pulsed acceleration past a fragmentation step; (ix) spatial focusing past a fragmentation step; (x) post-acceleration of fragment ion packets past a fragmentation step; (xi) steering past a fragmentation step; (xii) a combination thereof.

Implementations of this aspect of the disclosure may include one or more of the following features. In some implementations, the method further includes pulse-accelerating ion packets for a purpose selected from the group consisting of: (i) adjusting time focal plane of ion packets past said step of ion ejection; (ii) adjusting energy or energy spread of ion packets past said step of ion ejection; (iii) converting a continuous or a quasi-continuous flow past said ionization chamber, followed by a step of energy filtering of said pulsed accelerated ion packets; and (iv) a combination thereof. In some example, the step of ion packet refocusing comprises a step of converting wide (7-10 mm) and low divergent ion packets (<5-6 mrad) into smaller size (3-5 mm) and wider diverging (15-20 mrad) packets with conversion factor between 2 and 5. Optionally, the step of time-of-flight separation comprises time separation in electrostatic field of the group: (i) of linear field free TOF analyzer; (ii) of at least one ion mirror; (ii) of planar fields of two ion mirrors; (iv) at least one electrostatic sector; (v) a combination thereof.

The details of one or more implementations of the disclosure are set forth in the accompanying drawings and the description below. Other aspects, features, and advantages will be apparent from the description and drawings, and from the claims.

DESCRIPTION OF DRAWINGS

Various embodiments of the present invention together with arrangement given illustrative purposes only will now be described, by way of example only, and with reference to the accompanying drawings in which.

Like reference symbols in the various drawings indicate like elements.

DETAILED DESCRIPTION

Ion Packets Past So-EI Source

Figure 1:
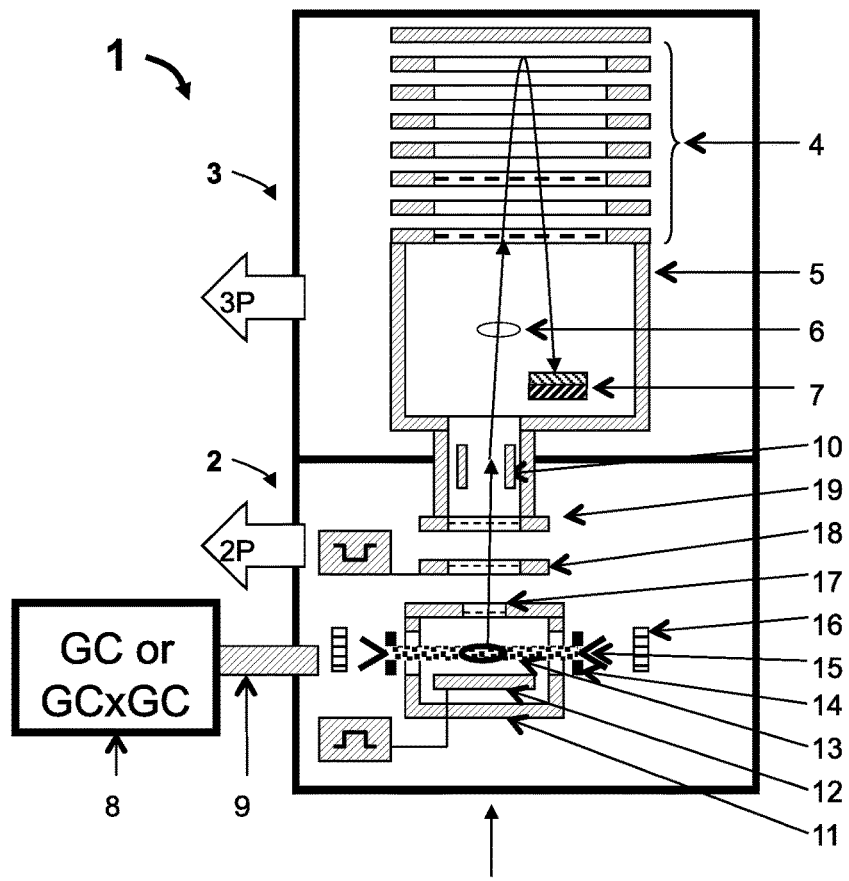
FIG. 1 depicts a time-of-flight mass spectrometer TOF-MS with semi-open electron impact (so-EI) source and singly reflecting TOF mass analyzer.

Referring to FIG. 1, a GC-TOF apparatus 1 is shown having a semi-open EI (so-EI) source 2 and a singly reflecting TOF MS 3. A sample mixture is separated in time by gas chromatograph 8 (GC or dual stage GC×GC) and is delivered into the so-EI source 2 through a GC column heated within hot transfer line 9. An electron beam 13 ionizes the sample and accumulates ions within an electrostatic well of the electron beam 13. An electrical pulse is applied to repeller 12 to drive the ejection of ion packets into TOF MS 3 at a 10 kHz-30 kHz frequency. For details of standard GC-TOF we refer to WO2013163530 application, which is incorporated herein by reference.

The key features of the so-EI source 2 include: (a) the source chamber 11, which has a limited total opening (i.e. limited to between about 0.1 cm² and 1 cm²)—the primary opening of the source chamber 11 is an extraction aperture 27 in an extraction electrode 17—for maintaining a higher sample concentration and for improving a sample-to-chemical-background ratio; and (b) slits 14 in-front of an electron emitter 15 that are biased at a positive potential (relative to electrodes surrounding ionization volume) for confining positive ions along the direction of the electron beam 13 and for drawing out secondary electrons.

Figure 2:
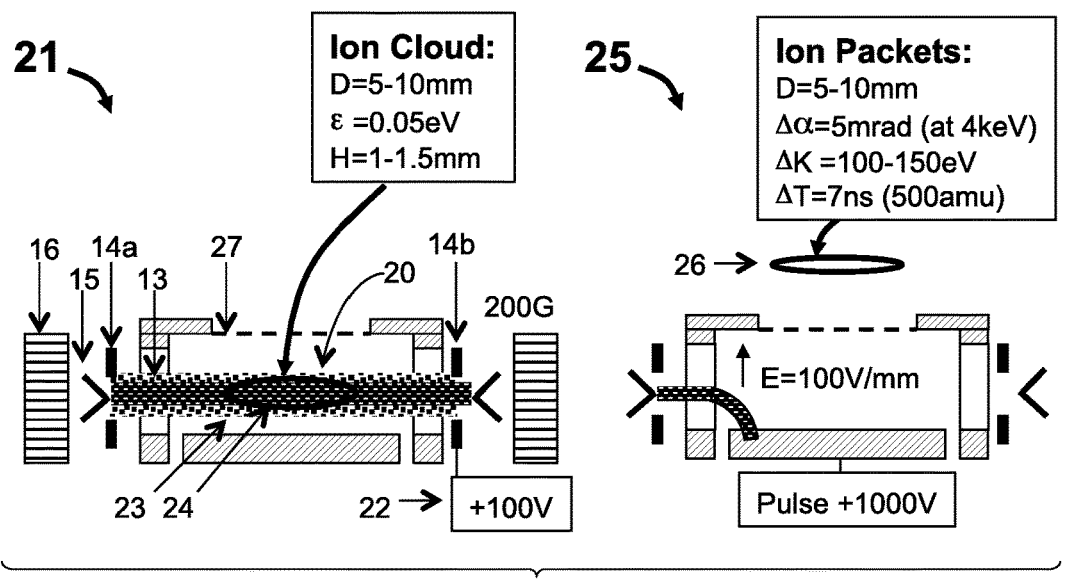
FIG. 2 describes main characteristics of semi-open EI source (i.e. limited opening and positive bias on electron beam slits, so as shows parameters of ion packets determined in authors measurements)

Referring to FIG. 2, expanded views of the so-EI source 2 at an accumulation stage 21 and at an ejection stage 25 are depicted, along with experimentally-measured ionic parameters. All the measurements were taken using a so-EI source 2 with 0.75 cm$^2$ opening, a 60 cm long reflecting TOF analyzer with a 1.5 m flight path at 2.5 kV acceleration and while measuring ionic signals on TOF detector 7 (shown in FIG. 1).

In the accumulating stage 21, an electron beam 13 is emitted by hot filament electron emitter 15, extracted by a front slit 14a, and accelerated to 70 eV energy within an ionization space 20 between a repeller plate 12 and an extraction aperture 27 of the extraction electrode 17 (the extraction aperture 27 is covered by a mesh, which is illustrated as a dashed line in FIG. 2). Electron beam 13 is confined along magnetic lines of magnets 16 having a 200-300 Gauss field strength. The analyzed sample is injected via transfer line 9 within the helium carrier gas, typically at 1 mL/min flow. The sample and Helium gas are introduced into the ionization space 20 and their concentration is defined by the gas conductance of the extraction aperture 27. Keeping the opening area of the extraction aperture 27 between 0.1 cm$^2$ to 1 cm$^2$ creates a helium conductance between 3 and 30 L/s, with conductance for analyte molecules being lower by a square root of an analyte mass. Such arrangement provides between a10-fold and a 100-fold increase in ionization efficiency compared to a fully open source. Further reduction of aperture size, however, is limited by multiple negative processes, such as slowing down the source reaction time (e.g., for GC×GC), building up of space charge, losing ion accumulation properties, and excessive scattering of ion-on-gas at ion ejection. A 70 eV electron beam ionizes sample molecules, thus forming an ion cloud 24 and secondary electrons 23. The secondary electrons 23 stay confined within the same magnetic lines that confine the electron beam 13. Both the primary electron beam 13 and the magnetically locked secondary electrons 23 form a negative potential well that traps the ions. A strong positive bias on both slits 14 (in FIG. 2, the positive bias is clearly illustrated at the back slit 14b) locks ions in the electron-beam direction and draws in the secondary electrons 23, which in turn makes the well shallower and promotes helium ions leaving the e-trap. As a result, analyte ions are fully trapped, while plasma concentration is notably reduced, which helps at the next stage of ion packet ejection 25.

Parameters of the ion cloud 24 and of the ion packets 26 are strongly improved in so-EI source compared to open EI sources. Additionally, parameters of the ion packets 26 strongly improve when both slits 14 have a positive bias compared to the source chamber 11, the repeller electrode 12, the extraction electrode 17, and the surrounding electron beam 13. The positive bias is depicted by power supply 22 applied to back slit 14b (but is preferably also applied to the front slit 14a). All the measurements refer to bias between about +20V and +100V on the front slit 14a and between +50V to +300V on the back slit 14b. Estimates of diameter D of the ion cloud 24 (which is orthogonal to a TOF axis) are made accounting for the size of the extraction aperture 27 and the measured ion packet 26 diameter D=5 mm-10 mm, determined from deflection profiles (using lens-deflector 10 in FIG. 1), while modeling ion focusing in the lens-deflector 10. Such calculations also account for the later-measured angular spread. Axial energy spread (along the TOF axis) of the ion cloud 24 is measured as 0.1 eV, assuming the domination of the turnaround time at small acceleration fields E<<100 V/mm in the source. Ion packet 26 angular spread was measured as Δα=6 mrad at 3 keV mean energy (corresponding to Δα=5 mrad at 4 keV), while installing additional collimators and measuring the deflection profiles. The radial energy spread is calculated from the angular divergence as 0.05 eV. Nearly thermal (50 meV at 300° C. source temperature) energy spread is explained by "cold plasma" conditions in the source. The energy spread of the ion packets 26 is measured as ΔK=100-150 eV via packet time spreading at time-of-flight defocusing (varying mirror potential), assisted by TOF MS simulations. The ion cloud height H=1-1.5 mm is calculated from the ion packet energy spread ΔK at an acceleration field of 100 V/mm. Ion packet time spread ΔT=7 ns for 500 amu ions is measured on the TOF detector 7 at optimal TOF conditions while using strong peaks without isobaric interferences and confirming the ΔT$^2$~m/z rule/relationship for smaller ion masses. In our measurements, we also confirmed ion accumulation properties of the so-EI source 2 up to 500 μs accumulation times. Using pulse periods up to 500 μs has not affected sensitivity and TOF resolution.

Sensitivity of so-EI-TOF has been measured S=150 ions/fg while injecting hexachlorobenzene (HCB) at loads from 100 fg to 10 ng into the GC column of GC 9. LOD measurement was assisted by examining detection of minor HCB isotopes. The typical sensitivity is LOD=100 fg for reliable identification with NIST library and from 20 fg to 30 fg for detecting major mass peaks (compound dependent).

For comparison, the same measurements at small or zero slit bias voltages have confirmed significant deterioration of ion packet parameters. Peak time width widens approximately 2-fold, and axial and radial energy spreads widen 3-fold to 4-fold. Additionally, Ion cloud height widens 1.5-2 times.

To support the thesis of so-EI source 2 advantage, we made similar measurements for open EI source from a Pegasus GC-TOF: ion packets beyond a standard open EI source have a time width of 30-40 ns at m/z=300 (compare to the 5 ns time width for so-EI). The diameter of the ion packets 26 is comparable to the source opening and detector size (25-30 mm compared with 5-10 mm in so-EI). The beam is strongly diverging (10-20 mrad compared with 5 mrad in so-EI).

These measurements confirmed that a so-EI provides much better ion packet parameters compared to a standard open source and that a positive bias on the slits 14 provides further significant improvement. Such dramatic improvement of ion packet parameters makes the so-EI source 2 compatible with TOF analyzers of smaller acceptance, such as MR-TOF (forming a so-EI-MR-TOF) and various so-EI-TOF-TOF tandems with CID and SID cells, which were non-practical and unthinkable before. The next question comes, is it worth troubles?

Rationality for So-EI-MR-TOF

The detection limit of GC-TOF employing a semi-open Electron Impact ion source 2 (so-EI) and a low resolution TOF is primarily limited by mass spectral interference caused by chemical noise and matrix ions, rather than by the number of generated ions. The so-EI source 2 provides very high efficiency of ionization, approaching 100-150 ion/fg on the TOF detector 7. At such sensitivity, 1 fg sample load provides sufficient ionic signal for detection. However, when combined with a low resolution analyzer (R≈1-2K), the detection limit (LOD) of the instrument is limited to 50-100 fg, primarily because of mass spectral interference with chemical background and with matrix ions. Statistical fluctuations of background signal do not allow distinguishing weaker analyte signals. Inventors arrived at the conclusion that both sensitivity and dynamic range of GC-TOF are expected to improve with instrument specificity, either at higher TOF resolution and/or with MS-MS features. Contrary to prior art knowledge, inventors found that so-EI source 2 generates low divergent ion packets ($\Delta\alpha$=5 mrad at 4 keV) which can be made compatible with the acceptance of multi-reflecting TOF analyzers (i.e. fitting an acceptance level that is notably smaller than singly reflecting TOF), provided that an optimized ion optical coupling is utilized. Thus, relatively wide (5-10 mm) ion packets 26 beyond the so-EI source 2 still could be refocused to fit the MR-TOF analyzer acceptance.

Inventors further found that the overall ionization and transfer efficiency of so-EI-MR-TOF is much higher compared to the alternative GC MR-TOF arrangement with a closed EI source coupled to the MR-TOF with an orthogonal accelerator (150 ion/fg compared to the closed EI ionization and transfer efficient of 1-3 ion/fg), which makes so-EI-MR-TOF a preferable solution to accomplish LOD improvement. Additionally, so-EI-MR-TOF is much less complex since it does not require transfer optics or an orthogonal accelerator. Thus, the so-EI-MR-TOF is the right way for solving both set problems: (a) improving LOD and (b) lowering instrumental complexity and cost.

Inventors further found that using a positively-biased slit 14 in the so-EI source 2 drops the time spread of ion packets 26 between 2-fold and 3-fold. When using an accelerating field of 100-200 V/mm, ion packet time width could be reduced to 5 ns at 250 amu and to 7 ns at 500 amu. Inventors further found that ion cloud thickness is small enough ($\approx$1.5 mm) and such accelerating fields allow for a moderate energy spread (200-300 eV), staying within the energy tolerance window of MR-TOF analyzer (7-10%) at an acceleration voltage above 4-5 kV. The combination of ion packet parameters allows obtaining R=20K resolution within a moderate size MR-TOF analyzer providing over a 10 m flight path and at a 400 µs flight time for 1000 amu ions. Inventors further found that the so-EI source 2 can sustain ion accumulation for a long period (400 µs) without affecting spectral quality for NIST identification. Analysis of other ion packets parameters and simulations of MR-TOF for such ion packets have shown that resolution of GC-MR-TOF is primarily limited by the time spread of the so-EI source 2, rather than by analyzer aberrations. Because of the medium (for MR-TOF) resolution, weaker mechanical tolerances are allowed and such MR-TOF analyzers can be made of low cost. Thus, a detailed study of ion packets' initial parameters led to the proposed: (a) effective coupling of the so-EI source 2 to MR-TOF analyzer; and (b) low-cost MR-TOF analyzer with lower mechanical tolerances compared to prior art GC-MR-TOF.

Novelty of the so-EI-MR-TOF combination is supported by the following arguments. The so-EI source 2 has been recently introduced in WO2013163530, which is incorporated herein by reference, for singly reflecting TOF having a large acceptance. Thus, known GC-TOF solutions could not operate with the excellent parameters of the so-EI source 2. Combining of so-EI source 2 to a high resolution MR-TOF was not envisioned in WO2013163530, because prior knowledge has taught that such combination would introduce unnecessary complications, provided poor resolution, and introduced severe ion losses. In the opposite, though, Inventors have discovered the importance of high resolution for LOD improvement, invented a compatible so-EI-MR-TOF combination, disclosed such a combination, and, as shown below, provided multiple effective solutions for such coupling.

Coupling of So-EI Source to MR-TOF

Figure 3:
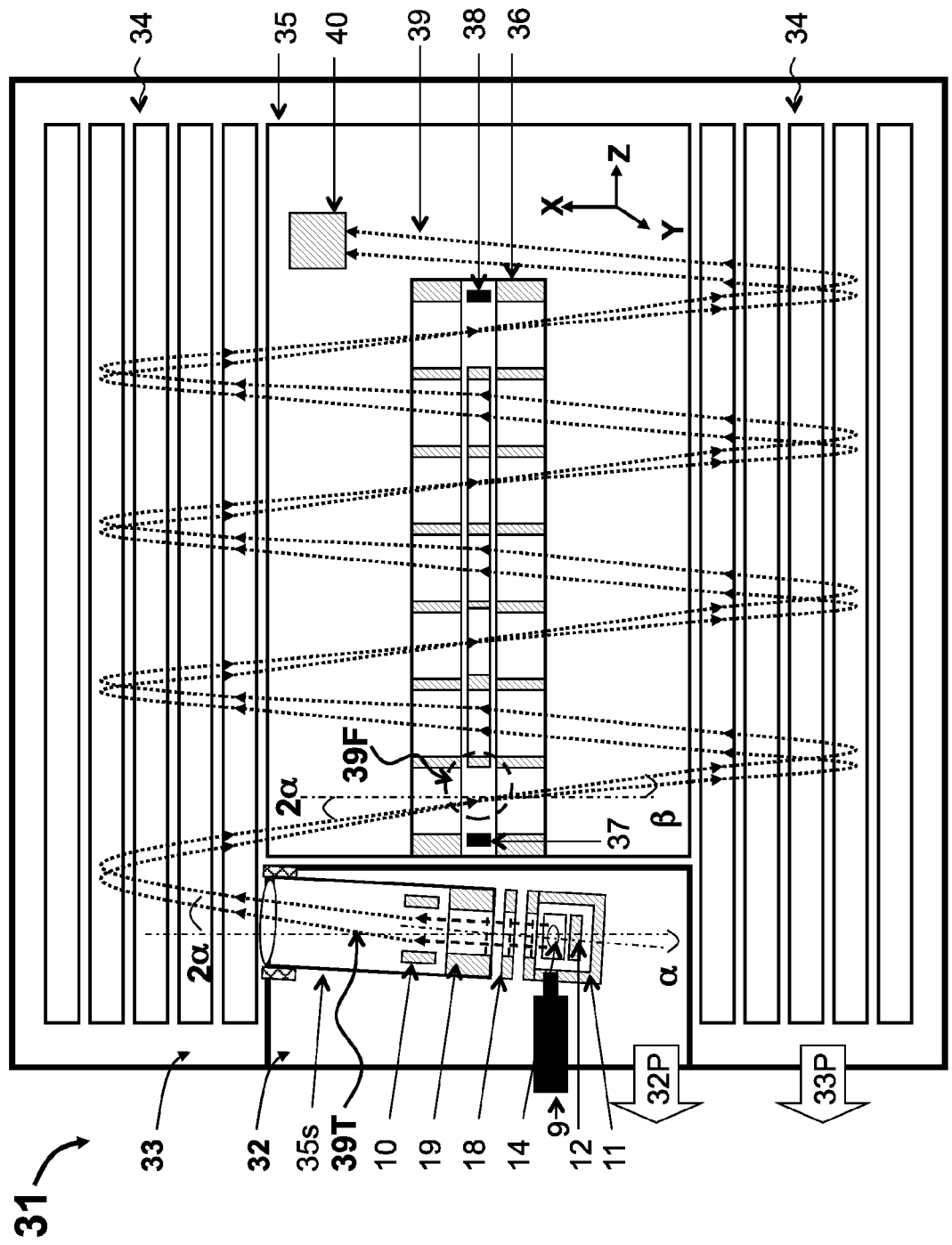
FIG. 3 depicts a GC-MR-TOF apparatus of the present invention where so-EI source is coupled to MR-TOF analyzer with isochronous interface based on ion beam refocusing and steering.

Referring to FIG. 3, an embodiment 31 of the so-EI-MR-TOF combination of the present disclosure incorporates a semi-open electron impact (so-EI) source 32 into a multi-reflecting time-of-flight analyzer 33 (MR-TOF). The MR-TOF analyzer 33 has a pair of parallel gridless ion mirrors 34 separated by a drift space 35 that is floated at acceleration potential, a set of periodic lens 36, a first end deflectors 37 and a second end deflector 38 (both optional), and a time-of-flight detector 40 (which is preferably a detector with extended dynamic range as described hereinafter). The so-EI source 32 is incorporated into a differentially pumped chamber as shown by arrows 32P and 33P, which depict separate turbo-pumps. The so-EI source 32 comprises an ionization chamber 11 having a total opening between about 0.1 cm$^2$ and 1 cm$^2$, an electron emitter 15 (shown in more detail in FIGS. 1-2) that emits an electron beam oriented orthogonal to drawing plane, at least one (preferably two) positively-biased electron slits 14, and a pulse accelerating plate 18. The so-EI source 32 is adapted with collimator 19, with a lens deflector 10, and with a drift space extension 35s.

The analyzer 33 may be either planar as shown in FIG. 3 or cylindrical as described in WO2011107836 (and incorporated herein by reference) for increasing a number of reflections within a compact-sized analyzer 33 for flight-path and flight-time extensions. The analyzer 33 may have ion mirrors 34 with third order energy focusing as described in WO2005001878 (which is incorporated herein by reference) or of higher order focusing as described in WO2013063587 (which is also incorporated herein by reference). Preferably, the analyzer is constructed using a low cost manufacturing technology, using aluminum mirrors coated with nickel phosphor.

Multiple conditions should be satisfied to obtain the desired range of the resolving power (about R=20K–25K). To accommodate so-EI ion packets with 10 ns time spread at about 1000 amu, about 25-50 mm*mrad emittance (at 4 keV), and 200-300 eV energy spread, the MR-TOF analyzer 33 should have at least about a 500 mm cap-to-cap distance and at least about a 4 keV acceleration voltage. It is more preferable using a higher acceleration voltage (up to 10 kV, practical limited due to about twice higher voltage on one of mirror electrodes) and using a larger cap-to-cap distance up to about 1 m-1.5 m. The flight path of the analyzer 33 should be extended to at least about 12 m-15 m, and the flight time should be extended to at least about 400 µs-500 µs.

To secure the desired resolution and to prevent ion losses, the ion injection scheme should generally match the ion beam emittance of the so-EI source 32 to the acceptance of the MR-TOF analyzer 33 and to minimize time-of-flight aberrations corresponding to ion beam focusing and steering in lens deflector 10, focusing in periodic lens 36, and steering in the deflectors 37 and 38. Estimations show that without such matching the width of the periodic lenses 36 in a Z-direction is required to be too large to reach the required total flight path length, and that TOF aberrations due to a large ion packet Z-directional width enlarge the ion packet time spread by a value comparable with the initial time spread provided by the so-EI source 32.

In an embodiment, in detail, the preferable scheme of matching is as follows. Referring to FIG. 3, ion packets follow ion trajectories 39 starting from the so-EI source 32. To ensure that the time front of the ion packets is parallel to a Z-axis, the so-EI source 32 is tilted by the angle $\alpha$ with respect to an X-axis. The lens-deflector 10 bends the ion packet trajectory to the same angle α (resulting in the trajectory being offset from the X-axis by 2*α). This scheme of aligning ion packet time front with the ion mirror is further described in WO2007044696 (disclosing an OA-MR-TOF), which is incorporated herein by reference. Moreover, in the considered coupling scheme of combination embodiment 31, the lens-deflector 10 focuses ion trajectories 39T to an intermediate spatial focus 39F between end deflectors 37 and 38 enabling an avoidance of time spread at the first end deflector 37 from the angle 2α to the angle β (notably, angle β matches an ion trajectory inclination in the periodic lens 36). A combination of the lens deflector 10 and the first of the set of periodic lenses 36 (combined with the deflector 37) simultaneously provides transformation of a wide ion packet produced by the so-EI source 32 to the narrower ion packet at the position of the first end deflector 37 (in which the ion packet width is determined by the angular divergence of ions from the so-EI source 32 and by the flight path length from the so-EI ion source 32 to the first end deflector 37). Then, the set of periodic lenses 36 refocuses ion trajectories 39 to the second end deflector 38 preventing ion packet from tilting in the second end deflector 38 and, thus, allowing arriving of the time front of the ion packets to the detector 40 in a position parallel to the detector's surface plane independently of excitation of the second end deflector 38. This described scheme still does not prevent tilting of ion packet time front for ions starting from the so-EI ion source 32 with an angular divergence.

Figure 4:
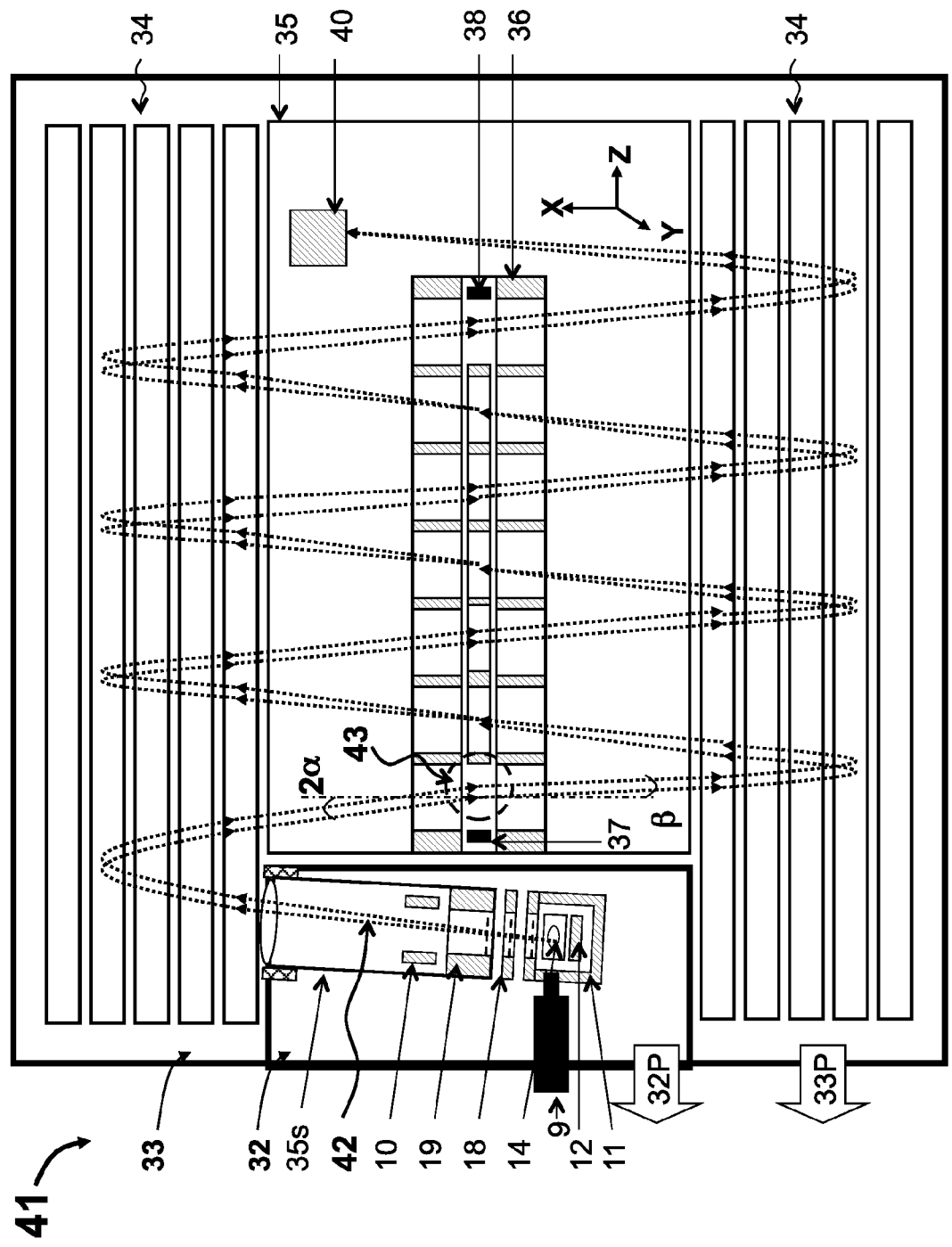
FIG. 4 depicts a GC-MR-TOF apparatus of FIG. 3 at different method of ion packet focusing and steering.

Referring to FIG. 4, an embodiment 41 of an so-EI-MR-TOF combination of this disclosure differs from embodiment 31 only in its ion trajectory focusing properties. Ion trajectories 42 start from so-EI ion source 32 with an angular spread in the Z-direction and form packets of a finite width (typically of about 4-5 mm) as shown by zoom region 43 positioned within the first end deflector 37, such that ion deflection from the angle 2α to the angle β necessarily tilts the time front of the considered ion packet. However, any tilt remaining at the position of the second end deflector 38 can be eliminated by additional packet tilting by this second end deflector 38, so that ion packet arrives to the detector 40 with a time front parallel to the surface of this detector 40. Alternatively, instead of the second end deflector 38 tilting ion packets, the surface plane of the detector 40 can be mechanically tilted. This method requires that the ion trajectories 39 of FIG. 3 were focused to the surface of the detector 40, instead of to the position of the deflector 38.

Figure 5:
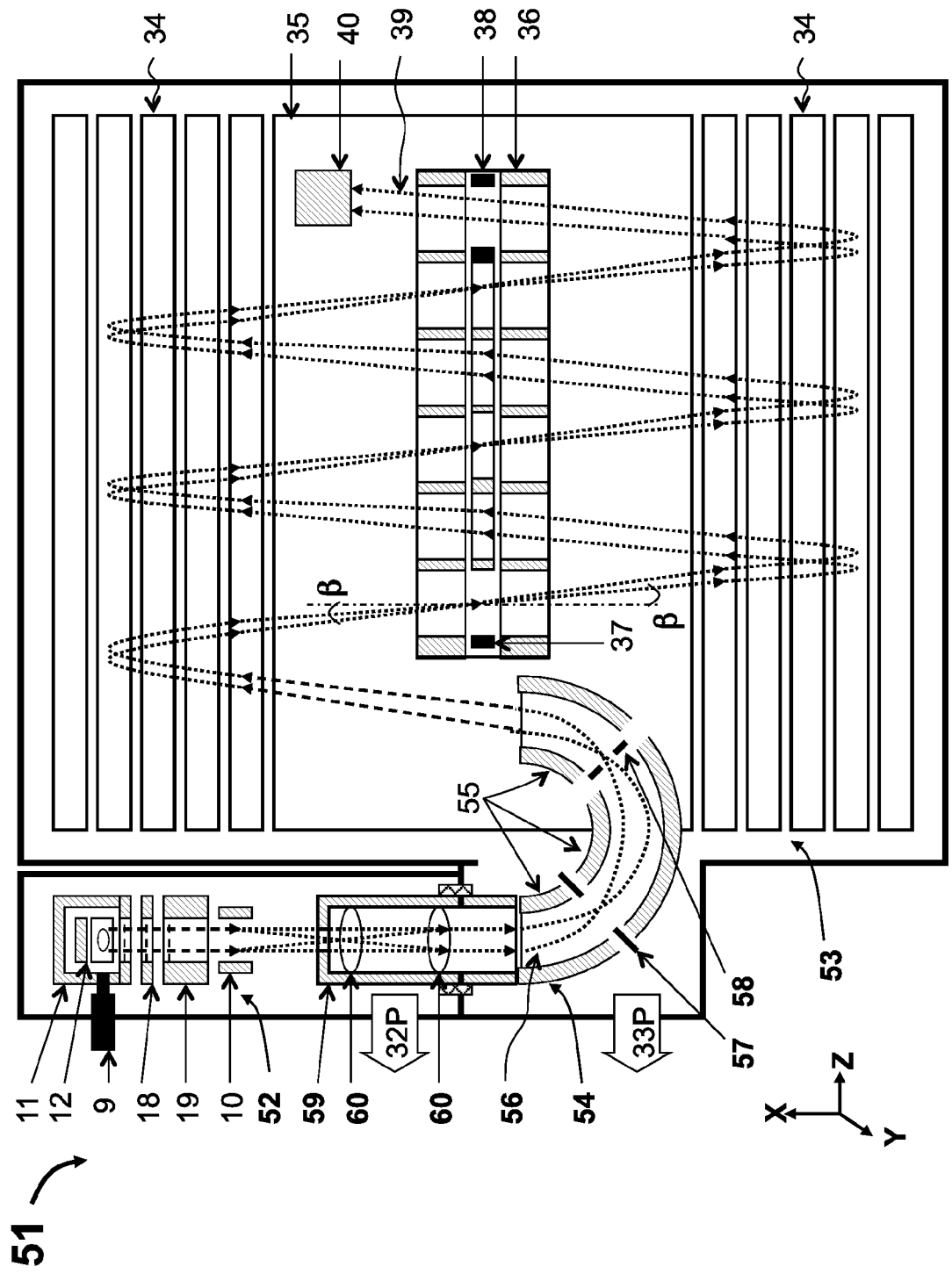
FIG. 5 depicts an alternative configuration of so-EI with MR-TOF analyzer employing a curved isochronous inlet.

Referring to FIG. 5, another preferred embodiment 51 of the so-EI-MR-ROF combination of this disclosure provides easier access to the so-EI source 52 and also provides energy filtering at the ion injection into the MR-TOF analyzer 53. Both the so-EI source 52 and the MR-TOF 53 include similar components to those components previously described regarding embodiment 31 (accordingly, FIG. 5 utilizes much the same part-numbering). The source 52 is coupled to the MR-TOF analyzer 53 via an isochronous curved inlet (C-inlet) 54, designed for ion trajectory steering at about 180°-β angle, where β is the tilt angle (offset from the X-axis) of ion trajectories 39 in the MR-TOF analyzer 53. The particular embodiment of C-inlet 54 of FIG. 5 includes three sets of electrostatic sectors 55 separated by apertures 57 and 58. One of the apertures (for example, the second aperture 58 in FIG. 5) is placed in the plane of spatial focusing, which allows for the filtering of ion energy of a few percent without spatial ion losses. Optionally a telescopic set of lenses 60 is installed prior to C-inlet 54.

There are considerations which should be accounted for in the design of the C-inlet 54. The curved inlet moves the time-of-flight focus, and it is preferable include a free-flight region 59 upstream of the C-inlet 54. Though the C-inlet 54 may serve as a differential pumping tube, it is more practical to utilize a differential aperture in the floated drift region 59 for this purpose, which allows setting the C-inlet 54 in the same differential pumping stage as the analyzer, evacuated by turbo-pump 33P. Additionally, it is preferable to deflect intense helium ion beams by a lens deflector 10 prior to injecting ions into the C-inlet 54 in order to minimize surface contamination by ions with wrong energy levels. The C-inlet 54 may be used for fine adjustment of the position and angle of the ion packets at the MR-TOF entrance by voltage adjustment on Matsuda plates, which work as cap electrodes the around electrostatic sectors 55. The inventors provide further details on such an adjustment scheme in WO2006102430, which is incorporated herein by reference.

Again referring to FIG. 5, another improvement of the scheme 51 involves inclusion and utilization of a set of telescopic lenses 60. The lens set 60 is tuned to form a spatial focus at the position of the energy filtering aperture 58 with variable angular ion packet spread at this position. This variation provides a necessary matching of the final ion beam width at the exit from the C-inlet 54. The second order time aberrations, originating in the lens set 60 due to the ion packet width, can be compensated by aberrations of the opposite sign that are created by the curved C-inlet 54 to eliminate time spread due to both tilting of the ion packet time front and to the time aberrations.

Exemplar apparatuses and methods of FIGS. 4-5 provide an optimal coupling between so-EI source 32, 52 and the MR-TOF analyzer 33, 53. This optimal coupling adopts the so-EI source spatial emittance to the MR-TOF analyzer acceptance while also optimally refocusing the ion beam for improved transmission and minimizing time spreads at least to the first order of the Taylor expansion T|Y=0, T|Z=0, T|a=0, and T|b=0 (where Y and Z are transverse spatial spreads and a and b are transverse angular spreads of the ion packets). Multiple other injection systems which effectively and isochronously adopt an so-EI source to an MR-TOF analyzer are also disclosed. Such additional disclosed interfaces include the following elements: (i) a differentially pumped chamber, accommodating an ion source and placed between said ion mirrors; (ii) an isochronous set of curved electrostatic sectors for external mounting of the ion source; (iii) an isochronous set of curved electrostatic sectors for displacing ion trajectory; (iv) an energy filter composed either of electrostatic sectors or deflectors combined with a spatial-focusing lens; (v) a lens deflector with a pulsed power supply for deflecting helium ions or for crude mass selection; (vi) a gridless ion mirror placed behind the ion source; (vii) a curved field accelerator built into the ion source for isochronous spatial focusing; (viii) a differential aperture placed at a plane of spatial focusing and followed by a spatial-focusing lens; and/or (ix) a telescopic lens system for reducing spatial packet size at the expense of widening angular spread.

Space Charge Limitations and Pulsing Schemes

High sensitivity of the so-EI source 2, 32, 52 is very likely to cause space-charge limitations at high sample loads in monograms (at or between about 1 ng-10 ng) range. Those effects are expected in both in the MR-TOF analyzer 33, 53 and in the so-EI source 2, 32, 52 at a full accumulation time of about 500 μs dictated by prolonged flight time in MR-TOF analyzer 33, 53. Let us utilize numeric calculations: At or about 100 i/fg sensitivity and at or about 10 ng sample loads per 1 second GC peak, the ion flux is expected to reach about 1E+9 ions/sec. If operating the MR-TOF analyzer 33, 53 at a standard regime (i.e. pulsing source at or about a 500 μs period), then the number of ions per shot reaches about 2E+6 ions/shot. Usually, EI spectra are presented by approximately 3-10 major peaks. Still, the number of ions per ion packet of a single m/z ratio may be as high as 3E+5 or 1E+6 ions. The MR-TOF analyzer 33, 53 is known to sustain resolutions up to about 300-1000 ions and to maintain an unaffected mass accuracy up to about 2-3E+4 ions per packet of a single m/z ratio.

Figure 6:
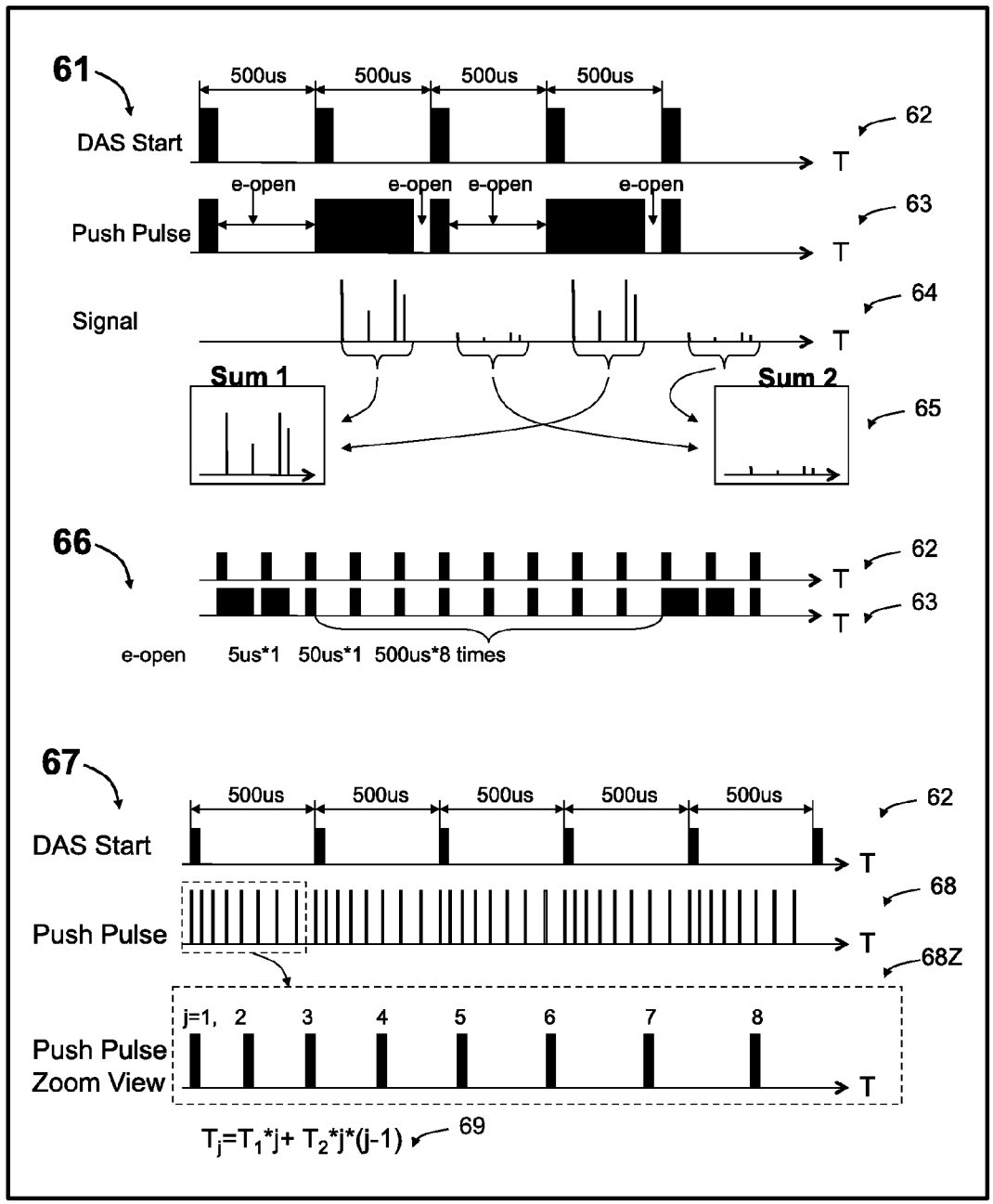
FIG. 6 depicts time diagrams for method of alternated pulse duration and method of frequent encoded pulsing—both designed for improving dynamic range of the so-EI-MR-TOF.

Referring to FIG. 6, there are presented time diagrams for an so-EI-MR-TOF combination operation in preferred modes. To solve the problem of the space-charge limitation, two solutions are disclosed: (a) alternated gain, controlled by the duty cycle of the ejecting pulse; and (b) frequent encoding pulsing at average frequency up to about 100 kHz.

Again referring to FIG. 6, the method of alternated gain 61 is depicted by a set of time diagrams in laboratory time T. Graph 62 depicts periodic starts of the data acquisition system (DAS) at or about every 500 μs. Graph 63 depicts timing of the push pulse (which may be, for example, applied to repeller electrode 12 in FIG. 3) applied with an alternated duty cycle. When the push pulse is applied, the electron beam is deflected as shown in the ejection phase 25 diagram of FIG. 2. The duration of the pulse off-time varies between shots, enabling a change to the duration of ion accumulation in the electron beam accompanied with a proportional change of the ion signal intensity. Variable mass spectral intensity is depicted in graph 64. Spectra are summed within at least two separate memory buffers as depicted in plot 65. Sum 1 will have a maximum signal intensity (strong shots), used to analyze weaker mass peaks, while strong peaks may saturate the space-charge limit of the analyzer, and so the dynamic range of the TOF detector, of the amplifier, and of the DAS. Those strong mass spectral signals will not saturate the data system at weaker shots (short electron-open time) and will be extracted from Sum 2 spectra. The scheme 66 shows that such alternation may be arranged with a minor compromise to the sensitivity, since weak shots (for example, between about 5 μs and 50 μs open time) may be acquired only once per 5-10 shots (there is enough signal statistics) while extending the dynamic range by two orders of magnitude, and strong shots (at 500 μs e-open time) may be acquired at an 80% duty cycle.

Again referring to FIG. 6, the method 67 of frequent encoded pulsing is depicted by time diagrams in laboratory time T. The graph 62 depicts periodic pulses, triggering a data acquisition system with a 500 μs time period, corresponding to the longest ion flight time in the MR-TOF analyzer. The graph 68 shows push pulses applied in strings of 500 μs duration. Details of the pulse string are more clearly seen in the zoom view 68Z. An exemplar string with unique time intervals is described by formula 69: $T_j=T_1*j+T_2*j*(j-1)$, where j is the pulse number in the string, $T_1$ is an average period between pulses, typically 10 μs, and $T_2$ is the increment which is chosen wider compared to peak width, say at 20 ns. WO2011135477, incorporated herein by reference, describes other details of spectral encoding and decoding. In high resolution MR-TOF analysis, the EI spectra are sparse enough to increase spectral population by between 30-fold and 50-fold. If necessary, the spectral population may be reduced by a partial mass filtering (which may be accomplished by, for example, the lens deflector 10 in FIG. 3) to maximize duty cycle at the expense of a moderate compromise in the mass range for target analysis.

In previous estimates, the maximal number of ions per packet (i.e. per mass peak per shot) was estimated as 1E+6 ions. A reduction of between 30-fold and 50-fold of ion accumulation time per shot would drop this maximal number to between 2-3E+4 ions per packet. This reduction is sufficient to maintain 1-2 ppm mass accuracy in the entire dynamic range.

Long Life Detector

In order to accommodate huge ion fluxes of the disclosed so-EI-MR-TOF apparatus embodiments, reaching up to 1E+9 ions/sec, the dynamic range and life time of the detector may be strongly enhanced utilizing the following novel combination.

Figure 7:
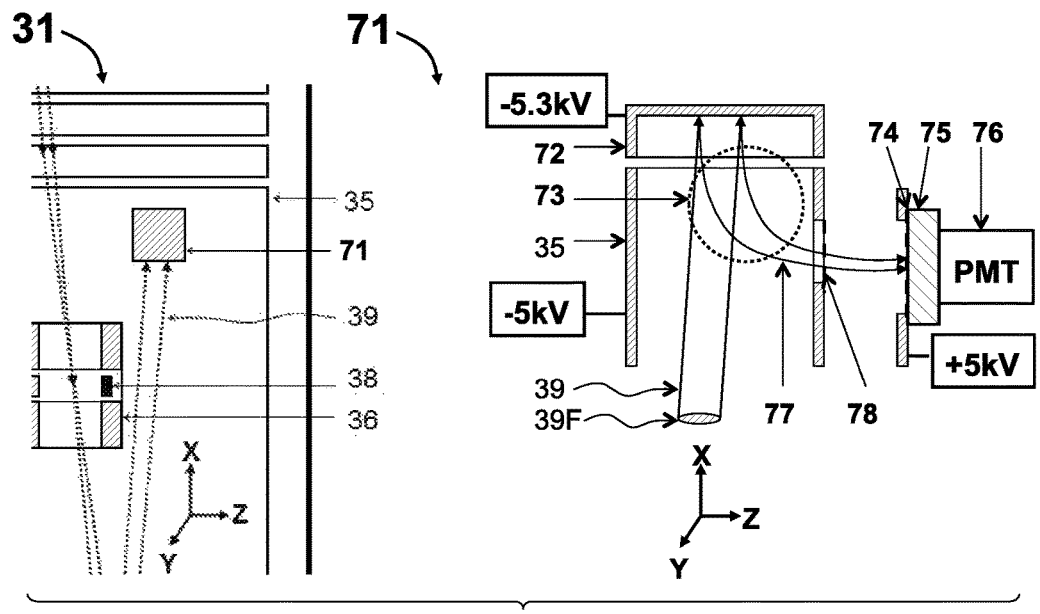
FIG. 7 depicts a TOF detector for improved dynamic range and life-time and suited for intensive ion packets in so-EI-MR-TOF of the present invention.

Referring to FIG. 7, an embodiment 71 of the improved time-of-flight detector comprises a conductive converter 72, magnets 73, a scintillator 75 that is coated or covered by a conductive mesh 74, and a photomultiplier 76. In a sense, the detector 71 is similar to a wide spread Daly detector, except the detector 71 embodiment has additional features that improve time-of-flight performance. FIG. 7 also presents a portion of the MR-TOF analyzer 31 of FIG. 3 having the detector 71 embodiment incorporated into the location of general detector 40.

In operation, the conductive converter 72 is installed in a Y-Z plane, normal to the X-axis and is installed parallel to the time front 39F of impinging ion packets along ion-packet trajectories 39. Also, the conductive converter 72 is floated negative by several hundred volts relative to drift space 35 of the MR-TOF analyzer 33 (for example, in detector 71 embodiment, there exists a 300V potential difference from a −5 kV potential at the drift space 35). Ions hit the conductive converter 72 having an energy between 5-6 keV (accounting for acceleration from the so-EI source), and then emit secondary electrons, with close to a unity of ion-to-electron efficiency for small molecules (typically under 500 amu) analyzed in GC-MS. Emitted electrons are accelerated by 300V difference between the conductive converter 72 electrode and the drift space 35 electrode while being steered along secondary electron trajectories 77 by a magnetic field formed by the magnets 73. The magnets 73 are installed to form magnetic lines along Y-axis to steer emitted electrons in the Z-direction. The bias is adjusted to correspond with the given strength of magnetic field (chosen between 30 to 300 Gauss) to provide electrons focusing onto the scintillator 75. The axis of the magnets 73 is preferably shifted from the axis of the ion beam to provide additional Y-directional confinement of the secondary electrons (accounting curvature of magnetic lines), while 90-degree magnetic steering provides natural electron confinement in the X-direction. Secondary electrons along their trajectory 77 are sampled through a mesh covered window 78 and are then accelerated to positively-biased scintillator 75. Higher biasing (up to +10 kV) of the scintillator 75 is preferred for higher signal gain, but may be limited for practical reasons. The scintillator 75 is a fast organic scintillator (for example, BC418 or BC422Q by St. Gobain) having a high electron-to-photon efficiency of at least 1 photon per every 60-100 eV of electron energy. Thus, a single secondary electron at 10-15 kV energy forms at least 15 photons. This allows reliable detection of almost every primary ion, in spite of limited efficiency of photon-collection (estimated in our experiments as approximately 20% efficiency) and in spite of a limited photon efficiency (25-30%) of the photo-emitter in the PMT 76.

Notably, conventional hybrid TOF detectors may employ an additional microchannel (MCP) stage in-front of the scintillator 75 in order to enhance the overall signal gain and may also employ a thin (1 μm) aluminum coating on top of the scintillator 75 to prevent scintillator-charging and to enhance photon-collection. Those two features strongly limit both life time and dynamic range of such conventional hybrid TOF detectors. The embodiment 71 of the disclosed detector alleviates those problems. Because the improvements disclosed for the embodiment 71 eliminate the need for MCP amplification, there is no saturation of an MCP (known to occur at 1E+7 ions/sec/cm$^2$ flux density), and the electron dose onto the scintillator 75 is reduced by between 100-fold to 1000-fold (since there is no MCP amplification). There is also no thin aluminum coating which might otherwise suppress fast electrons at low reproducibly. The embodiment 71 also, thus, also eliminates the problem of damaging the aluminum coating at large ionic doses. Instead, a deposited or covering thick metal conductive mesh 74 appears sufficient to provide electrostatic removal of the electron charge by surface discharges and leaks at 1 kV/mm at 0.3-1 mm cell size of the conductive mesh 74.

There are commercially available PMT amplifiers (for example. R9880U by Hamamatsu) that have an extended life time 300 Coulomb, measured by the output charge, while providing a relatively short (1.5 ns) rise time. At 1E+6 overall gain and 1E+9 ions/sec average ion flux, the output current is 160 μA (i.e. the detector 71 is expected to survive for 2E+6 seconds—almost 500 hours at maximal load and for at least a year at standard loads). With an external PMT coupling (say via glass tube for passing photons) the PMT module 76 could be replaced without venting the instrument. External PMT coupling also helps suppressing pick up from pulse generators in a frequent pulsing mode that has been described previously as illustrated in FIG. 6.

The linear range of the detector 71 (normally limited by output current to 100 μA by a standard resistive divider) could be improved. For example, the last few stages may be fed by a more powerful supply (at least several mA current limit) or by being controlled by active circuits. To enhance the dynamic range of the detector 71, last PMT stages 76 are connected to buffer capacitors. But those standard solutions may be insufficient for temporal peak signals. Further enhancement of the dynamic range is herein disclosed by using: (a) frequent encoded pulses in the source 2, 32, 52, which drops the detector maximum signal by two orders of magnitude; or (b) an alternated gain pulses, followed by amplifier with fast cut off and rapid recovery. Both solutions have been described previously in this disclosure and are illustrated in FIG. 6. The dynamic range may be further improved if: (a) using dual PMT with different efficiency of light collection; (b) taking signals from different PMT stages; (c) using preamplifiers with dual (triple) gain outputs; and (d) alternating either electron collection efficiency or PMT gain between shots.

Notably, the disclosed so-EI-MR-TOF instruments 31, 41, 51 would be non-practical and unthinkable if using (a) conventional (rare pulses) operation regime or (b) conventional TOF detectors with short life time (typically 1 Coulomb for standard MCP and non-sealed SEM). The proposed pulsing methods—encoded frequent pulsing or alternated gain scheme (in a co-pending application, incorporated herein by reference) and presently disclosed long life detector—do solve those problems and make the so-EI-MR-TOF 31, 41, 51 a practical solution for enhanced sensitivity and dynamic range of GC-MS analysis.

Soft Ionizing Sources

In an implementation, preferably, GC-MS instruments have at least some soft ionizing options in addition to the so-EI source 2, 32, 52. Approximately 30% of compounds in NIST library do not form a molecular ion, and their identification is enhanced by using soft ionization options. Here we propose several ways of coupling chemical ionization CI, Cold EI, and molecular generator to the so-EI-MR-TOF apparatus 31, 41, 51.

Figure 8:
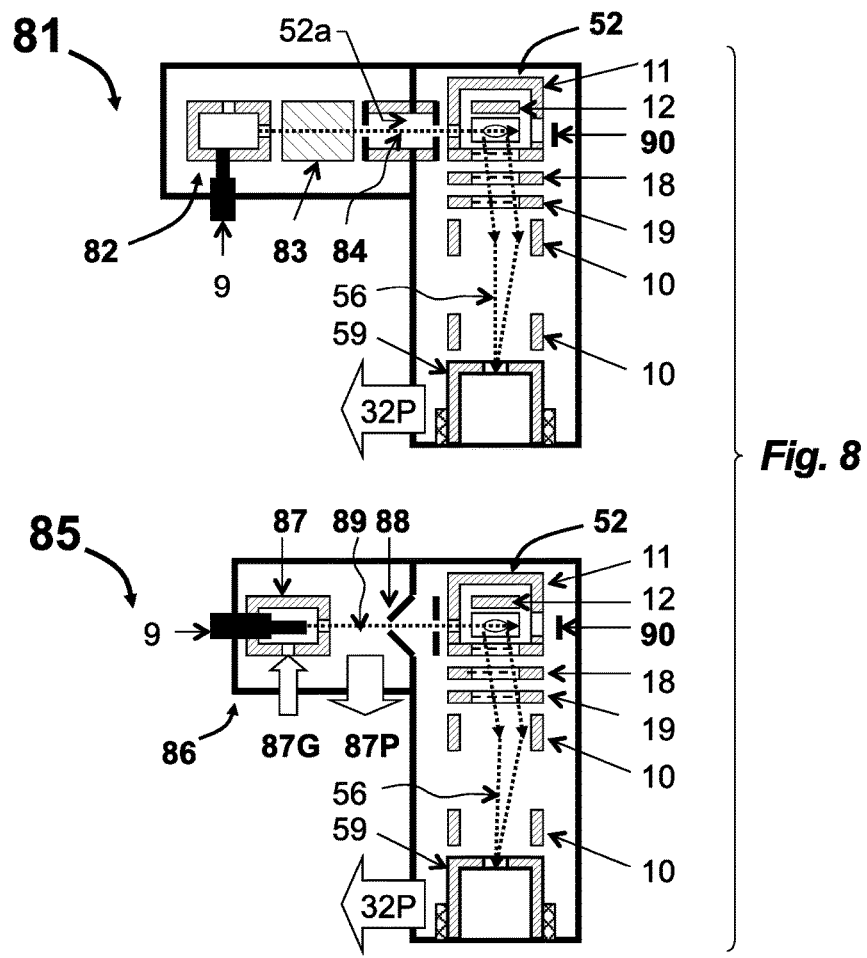
FIG. 8 depicts an embodiment with external CI source and with external molecular beam generator for soft ionization in so-EI source.

Referring to FIG. 8, there are shown two embodiments 81 and 85 of the present disclosure, wherein the so-EI source 52 is employed as an orthogonal accelerator for externally generated ions 84 or for externally introduced molecular beam 89. Both may employ a TOF, such as the singly reflecting MS 3 in FIG. 1 or the MR-TOF analyzers 33, 53 in FIGS. 3-5.

Referring to FIG. 8, one preferred embodiment 81 of GC-MR-TOF of the present invention includes the previously described so-EI-MR-TOF apparatus 31, 41, 51 with so-EI source 32, 52 and MR-TOF analyzer 33, 53 (which are not shown in FIG. 8). In addition, a CI source 82 is installed orthogonally to so-EI source 52 and is coupled via transfer optics 83, which preferably has a heated collimator. In operation, the CI source 82 forms the continuous ion beam 84, which is spatially focused by the transfer optics 83 onto the so-EI source entrance port 52a. The electron beam may be turned on in an attempt of accumulating externally generated ions within an electrostatic well of the electron beam. However, in the present embodiment we propose switching the electron beam off and relying of the conventional method of the orthogonal acceleration. A portion of the continuous ion beam 84 is pulsed accelerated by the repeller 12. Preferably, the energy of continuous ion beam 84 is maintained between 5 eV and 15 eV to minimize tilt of ion trajectory 56. Tilted ion packets are steered by a pair of lens deflectors 10 to align the packets trajectory 56 with the ion path in the MR-TOF analyzer 33, 53. Preferably, the pulsed acceleration is operated at frequent encoding to enhance the instrument's duty cycle. Though the method may compromise the duty cycle and resolution for CI analysis, it allows straight-forward alternating between soft CI and standard EI ionization methods in the so-EI-MR-TOF instrument 31, 41, 51.

Again referring to FIG. 8, yet another preferred embodiment 85 of GC-MR-TOF depicts a so-EI source 52 coupled with external molecular beam generator 86. The molecular beam generator 86 comprises a nozzle chamber 87, a port 87G supplying Helium gas at approximately 100 mL/min, a skimmer 88, and an additional pumping port 87P. Preferably, the additional pumping port 87P is connected to a differential inlet of the turbo-pump 32P, evacuating the source chamber (i.e. the same generator may be used as a molecular separator as described in WO2013163530, which is incorporated herein by reference). At proper gas dynamic settings (i.e. at a small-sized nozzle of approximately 0.1 mm, a 1 mm opening of the skimmer 88, and sufficient pumping 87P equaling at least 10 L/s and more preferably 70-300 L/s), the molecular beam generator 86 forms a well-directed molecular beam 89 of vibrationally-cold analyte molecules carrying the analyte molecules at 2-3 km/s velocity (with an estimated Mach number of two or three and a thermal velocity of helium carrier gas of 1 km/s). The beam is directed into the source chamber 11 of the so-EI source 52. The electron ionization of internal energy cold molecules is softer and forms much more intense molecular ions compared to the standard EI method. Thus, formed ions will retain an analyte velocity and are expected to have a notable energy level (for example, 14 eV at a velocity of 3 km/s for 300 amu ions). The continuous beam can be monitored by a collector 90, which resided within the so-EI source 52 beyond an exit aperture of the source chamber 11. Preferably, the total opening in the so-EI source 52 is about 1 cm² in order to maintain at 0.1-1 Tor gas pressure in the so-EI source 52 and to limit number of collisions between analyte molecules and residual gas (for example, to limit them to no more than a few). A portion of the continuous molecular beam 89 is pulse-accelerated by the repeller 12, and ion packets are deflected by a pair of lens deflectors 10 to align the packets trajectory with the ion path in the MR-TOF analyzer 33, 53. Preferably, the pulsed acceleration is operated at frequent encoding to enhance the instrument duty cycle. Though this disclosed method may compromise duty cycle and resolution of soft EI, it allows for straight-forward alternating between soft EI and standard EI ionization methods in the embodiments 31, 41, 51.

Figure 9:
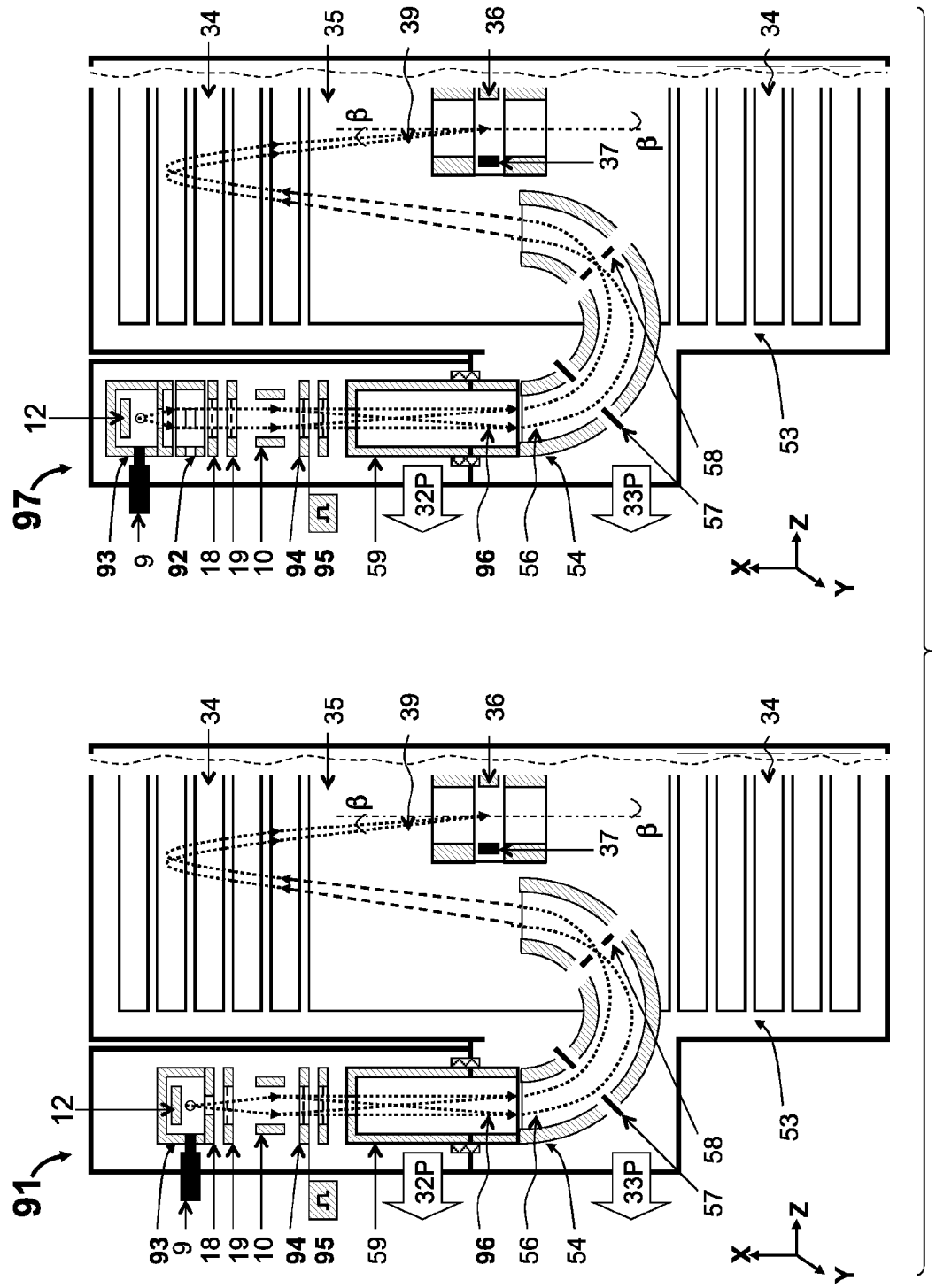
FIG. 9 depicts an embodiment with external CI source followed by a pulsed ion packet bunching and then by energy filtering in a curved isochronous sector interface, the latter described in co-pending application.

Referring to FIG. 9, another embodiment 91 of the disclosure comprises an MR-TOF 53 with curved inlet 54 as described in more detail above and as illustrated in FIG. 5. The embodiment further includes a chemical ionization source 93 forming a continuous ion beam and a pulsed accelerator (buncher 94) connected to a pulse generator 95. The continuous ion beam is spatially focused by a lens deflector 10 to arrange ion passage through the collimator 59 and to provide ion packet 39 focusing past the curved inlet 54. The buncher 94 (preferably located past the lens deflector 10) accelerates a portion of continuous ion beam. The packets are focused at an intermediate spatial focusing plane and are energy-filtered by a slit 58, thus accepting the packet portion suitable for the MR-TOF 53. Preferably, the buncher 94 is operated according to a frequent-encoded pulsing method. As described in a application (originally filed as U.S. 61/973,117 and incorporated herein by reference), the method allows reaching up to a 10-20% duty cycle for pulsed conversion.

Again referring to FIG. 9, yet another embodiment 97 of the disclosure includes a chemical ionization source 93 installed adjacent to so-EI source 92, wherein the so-EI source 92 acts as spatial focusing lens and in some embodiments may act as pulsed acceleration stage. The embodiment allows operating the same hardware set in both CI and EI modes. When using CI ionization, the so-EI source 92 transfers the ion beam. When using EI mode, neutral analyte molecules pass through the CI source 93 volume.

In both embodiments 91 and 97, the CI source 93 is promoted to eject either a continuous or a quasi-continuous ion beam. The pulsed accelerator (embodied as buncher 94) bunches the ion packets (alternatively or additionally, the repeller 12 of the so-EI source 92 may bunch the ion packets). The energy filter (embodied as a curved inlet 54) passes a portion of the ions that fit within an energy acceptance that matches the energy acceptance of the MR-TOF analyzer 53. Preferably, the pulses are applied at frequent time encoding (EFP) to enhance duty cycle of the analysis.

Embodiments 91 and 95 are described with additional detail in a aforementioned and incorporated co-pending application by the present inventors.

Conclusion on So-EI-MR-TOF

The so-EI source provides an approximately ten to hundred times brighter ion beam (comparing analyte signal per phase space) and several times shorter ion packets compared to conventional open EI source with ion accumulation in an electron beam. This disclosure has proposed multiple solutions for effective coupling of an so-EI source, including effective ion injection schemes for spatial and angular refocusing, isochronous schemes for reducing MR-TOF analyzer aberrations at the ion beam injection, solutions to problems of space-charge limitations within the so-EI source and within the MR-TOF analyzer, and has proposed a detector with extended life time and increased dynamic range for detecting large (i.e. up to 1E+9 ions/sec) fluxes. Without such novel disclosed solutions and without the disclosed bright so-EI source the EI-MR-TOF combination would be non-practical.

GC-MS-MS

Current limits of GC-MS sensitivity occurring due to the lag of specificity and the sensitivity of GC-MS can be improved by using specificity of MS-MS analysis in spite of additional spatial losses usually associated with duty cycle losses at sequential parent selection in MS1. GC-MS-MS analysis is distinct from other MS-MS analyses (such as LC-MS-MS in proteomics) because of high GC reproducibility and because of primary interest in target analyte compounds, wherein retention time and parent mass of target compounds are known prior to the analysis. Upfront mapping of parent masses per retention time allows selecting of a single or a very few parent ion masses, and then using MS-MS would not reduce signal intensity while strongly improving selectivity of the analysis.

The emittance of so-EI source is small enough to be compatible with TOF-TOF analyzers, if providing: (a) appropriate time and spatial focusing of parent ion packets; and (b) appropriate time and spatial refocusing and post-acceleration for daughter ion packets.

MS-MS features can be achieved in the so-EI-MR-TOF instrument if using a surface induced dissociation (SID) fragmentation cell, built into the MR-TOF analyzer or coupled via a curved isochronous inlet. WO2013192161 by present inventors (incorporated herein by reference) describes using the same MR-TOF analyzer for both MS stages. It also describes a comprehensive MS-MS (i.e. parallel or all-mass) achieved at moderate resolution of parent selection (R1≈100) with a 10-20% duty cycle, while using a novel multiplexing approach of non-redundant sampling (NRS) combined with frequent encoded pulsing (EFP).

MS-MS features can further be achieved with a collisional induced dissociation (CID) cell if making multiple accommodating steps, such as focusing of wide ion packet into a small size CID cell at moderate ion energy and accelerating and refocusing fragments. Multiple other means are disclosed for improving the scheme, such as a focusing reflector behind the so-EI source and a time-ion-selector built into the CID cell. The disclosed apparatus is also compatible with NRS and EFP methods for strong enhancement of duty cycle and dynamic range of the analysis.

Depending on the method arrangement, efficiency of MS-MS varies dramatically.

Below are disclosed several practical MS-MS setups for singly reflecting TOF and for MR-TOF analyzers.

Differentiation with Prior Art TOF-TOF

Various tandem TOF-TOF instruments have been developed for MALDI ion source as described U.S. Pat. Nos. 5,739,529, 6,703,608, 6,717,131, 6,300,627, 6,512,225, 6,621,074, 6,348,688, 6,770,870, 7,667,195, 8,461,521, WO2011028435, US2012168618, and WO2013134165, each of which is incorporated herein by reference. However, MALDI is an intrinsically pulsed source with extremely small spatial and energy emittance, and it forms primarily molecular ions, which makes them excellent for TOF-TOF.

EI sources have not been considered compatible with TOF-TOF because of their huge emittance, because of the expected metastable decay of EI-formed ions, and because of already formed fragment spectra, usually recovered by correlating fragments with chromatographic time.

TABLE 1

Comparing initial ion packet parameters between DE MALDI, standard open pulsed EI source, and recently introduce semi-open so-EI source:

| Parent ion parameter | units | MALDI | Open EI | So-EI |
|---|---|---|---|---|
| Mass | amu | 1000 | 500 | 500 |
| Non correlated spatial spread | mm | 0.1 | 30 | 10 |
| Angular spread at 5 kV | mrad | 5 | 17 | 5 |
| Non correlated time spread | ns | 1 | 25 | 5 |
| Energy spread | eV | 1 | 200 | 100 |
| Non correlated spatial emittance | mm * mrad | 0.5 | 500 | 50 |
| Non correlated energy emittance | ns * eV | 1 | 5000 | 500 |

To assess ion packet parameters in MALDI source we assume 100 μm laser spot, 1-2 ns initial ejection event, 500 m/s axial velocity, 150-200 m/s axial and radial velocity spread of the ejecting plume, and 300 ns delay before applying an extraction pulse with 1 kV/cm field strength. Before applying the extraction pulse, non-correlated time spread is assumed 1 ns, and energy spread is assumed 1 eV (i.e. $\Delta T * \Delta K = 1$ ns * eV). After the 300 ns delay, the pulse will expand for 30 microns, and the acceleration will induce a 30 eV energy spread and a 2 ns time spread. In spite of 60 ns * eV product, those spreads are strongly correlated, which is used for DE focusing as described in U.S. Pat. No. 5,760,393, U.S. Pat. No. 5,625,184, and U.S. Pat. No. 6,541,765 by Marvin Vestal et al (each of which is incorporated herein by reference). The non-correlated energy emittance stays 1 ns * eV. The angular divergence is defined by initial radial energy of 1000amu at 75-100 m/s velocity (i.e. 0.05 eV). After acceleration to 5 kV the full angular divergence becomes 6 mrad, and, thus, spatial emittance is 0.5 mm * mrad.

To assess ion packet parameters in MALDI source we assume 100 μm laser spot, 1-2 ns initial ejection event, 500 m/s axial velocity, 150-200 m/s axial and radial velocity spread of the ejecting plume, and 300 ns delay before applying an extraction pulse with 1 kV/cm field strength. Before applying the extraction pulse, non-correlated time spread is assumed 1ns, and energy spread is assumed 1 eV (i.e. $\Delta T*\Delta K=1$ ns*eV). After the 300 ns delay, the pulse will expand for 30 microns, and the acceleration will induce a 30 eV energy spread and a 2 ns time spread. In spite of 60 ns*eV product, those spreads are strongly correlated, which is used for DE focusing as described in U.S. Pat. Nos. 5,760,393, 5,625,184, and 6,541,765 by Marvin Vestal et al (each of which is incorporated herein by reference). The non-correlated energy emittance stays 1 ns*eV. The angular divergence is defined by initial radial energy of 1000 amu at 75-100 m/s velocity (i.e. 0.05 eV). After acceleration to 5 kV the full angular divergence becomes 6 mrad, and, thus, spatial emittance is 0.5 mm*mrad.

Thus, spatial and time-energy emittance of MALDI sources are smaller by three orders of magnitude compared to those in standard open EI sources and by two to three orders of magnitude compared to recently introduced so-EI sources. There are a few other differences. For example, the MALDI TOF operates at 20-30 kV acceleration while EI-TOF operates at 1-5 kV acceleration. And the MALDI source is floated while the so-EI is at a ground potential. Finally, the MALDI source is in vacuum while gas pressure in so-EI source is estimated between 0.1 and 1 mTor.

There exists a utility of TOF-TOF for EI source as a mean for improving analysis specificity. Inventors discovered that in spite of much larger emittance of parent ions, the emittance of fragment ions could be made comparable to those in MALDI-TOF-TOF, because the majority of beam spreading occurs in CID cell and at metastable recoil. The inventors further discovered that, to achieve acceptable parameters of fragment ions, one should apply a simultaneous spatial and time focusing at fragmentation cell and to make those cells as short as practically possible.

Estimates of Parent and Fragment Ion Parameters

Analysis and optimization of TOF-TOF schemes would require estimating ion packet parameters at various MS-MS stages, summarized in Table 2. For compatibility of the following numerical examples let us make such estimates. We assume parent ions of mass 500 amu and fragment ion mass 100 amu. We assume 5 keV ion energy in TOF analyzer and a 3 m flight path (L) in a 1 m long TOF analyzer. We assume parent energy prior to fragmentation being 500 eV, (i.e. parent ions move at 14 mm/μs velocity according to $V^2=2$ eU/m).

At soft fragmentation (post-source decay, collision with helium atom, or gliding collisions with a surface), the fragment average velocity remains about the same, which means 100 amu fragments move with 100 eV average energy. We assume maximum recoil energy at meta-stable fragmentation being 1 eV, which means that 100 amu fragment recoil at 1.4 mm/μs velocity in the center of mass. This causes +/−10% maximum velocity spread and a 10% width of velocity spread at half maximum ($V_{FWHM}=3\%$). This also means that 100 mrad angular divergence of fragments relative to parent trajectory occurs just after fragmentation. Accounting for post-acceleration from 100 eV energy to 5 keV energy, the fragment angular divergence drops as a square root of energy and becomes 14 mrad. Notably, the angular divergence of fragment ions at 1 eV recoil energy is independent of fragment mass and could be estimated by the square root of (1 eV/5000 eV).

When arranging the CID cell, we assume an adjustment of gas pressure P in the cell to induce one collision on average (i.e. portion of collided ions is equal to 1-1/e. The cross section of 500 amu ions is assumed at 100 $A^2$ (i.e. 1E-14 $cm^2$). Then, for n=2.7E+19 molecules/$cm^3$ at 1 atm, the condition of a single collision average occurs at length*pressure product L*P=3 cm*mTor.

We assume helium gas (m=4 amu). Accounting momentum conservation, collision of M=500 amu parent ion would cause m/M momentum and energy loss. This corresponds to approximately 4 eV collision energy in the center of mass. We assume such energy to be sufficient for inducing fragmentation of relatively small and already excited molecular ions. Maximum angular spread for the parent ion can be then estimated as +/−8 mrad at FWHM=8 mrad. However, in spite of low velocity and angular spread caused by the collision itself, the fragmentation is likely to occur at the same recoil energy of 1 eV, causing 100 mrad divergence in the fragmentation cell and 14 mrad divergence in the TOF analyzer. Notably, in divergence estimates, the gas collisions remain a small factor compared to fragment recoil, even for a small parent mass (down to 50 amu) and independent of fragment mass. Also notably, from the point of fragment scattering, a heavier gas could be used which allows smaller parent energies.

When arranging gliding collisions with a surface (SID), we assume a preservation of ion energy along the gliding ion path and a radial energy spread of 1 eV, which corresponds to a divergence of +/−50 mrad. Such divergence, combined with 1 eV recoil energy, is expected to cause 140 mrad angular divergence in the cell and 20 mrad divergence in the TOF analyzer.

The results of such estimates are presented in Table 2. At this point we highlight the following: though emittance of the primary beam beyond the so-EI source is 100 times larger than MALDI sources (i.e. 50 vs. 0.5), it is smaller than the emittance past the CID cell (200 mm*mrad).

TABLE 2

Summary of expected ion packet parameters

|  | units | TOF1 | Fragm Cell | TOF2 |
|---|---|---|---|---|
| Parent ion parameter | | | | |
| Mass | amu | 500 | 500 | 500 |
| Energy | eV | 500 | 500 | 5000 |
| Velocity | mm/µs | 14 | 14 | 45 |
| Packet width | mm | 10 | 2 | 3 |
| Angular divergence | mrad | 5 | 25 | 5 |
| Emittance | mm * mrad | 50 | 50 | 15 |
| Emittance (FWHM) | | 25 | 25 | 7.5 |
| Daughter packet parameter | | | | |
| Mass | amu | — | 100 | 100 |
| Energy | eV | — | 100 | 4600 |
| Velocity | mm/µs | — | 14 | 95 |
| Packet width | mm | — | 2 | 10 |
| Fragments spread in fragmentation cell | | | | |
| Maximum recoil energy in center of mass | eV | — | 1 | |
| Maximum recoil velocity | mm/µs | — | 1.4 | |
| Maximum recoil divergence | mrad | — | 200 | 30 |
| Recoil divergence (FWHM) | mrad | — | 100 | 15 |
| Emittance (assuming focusing to 2 mm) | mm * mrad | — | 200 | 30 |
| Emittance (2 mm) (FWHM) | mm * mrad | — | 100 | 15 |
| CID energy spread (500 amu and 4 amu gas) | eV | — | 0.8 eV | |
| CID max angular spread (no recoil) | mrad | — | 16 | 2 |
| CID max emittance (2 mm parent beam) | Mm * mrad | — | 32 | 4 |
| CID emittance (2 mm parent beam) (FWHM) | Mm * mrad | — | 16 | 2 |
| SID max energy spread (no recoil) | eV | — | 1 | |
| SID max angular spread (no recoil) | mrad | — | 100 | 14 |
| SID emittance (no recoil) | mm * mrad | — | 200 | 30 |
| SID emittance (no recoil) (FWHM) | mm * mrad | — | 100 | 15 |
| SID emittance (with recoil) (FWHM) | mm * mrad | — | 140 | 20 |

Figure 10:
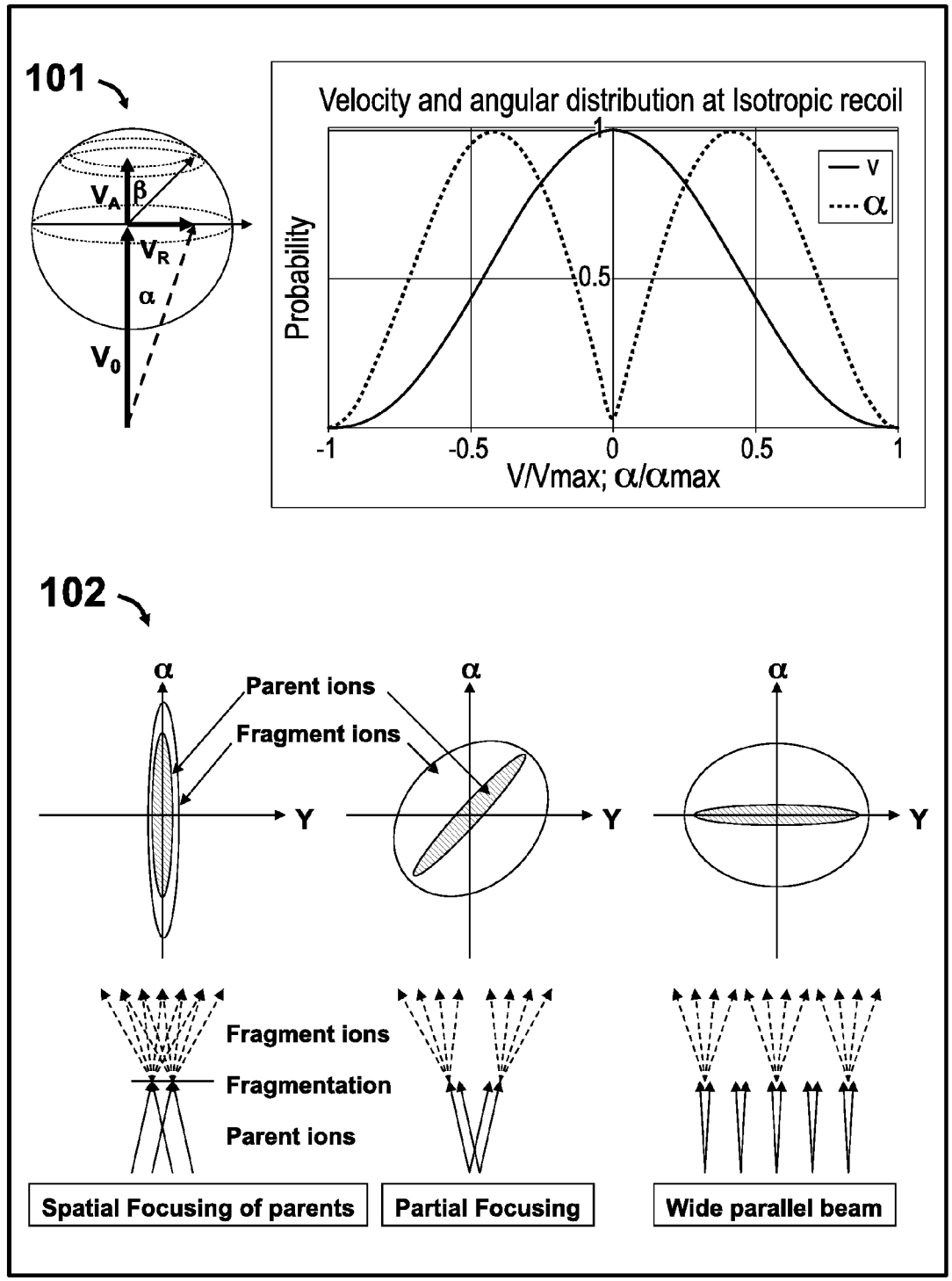
FIG. 10 illustrates a method of simultaneous spatial and temporal focusing of ion packets into a fragmentation cell for tandem TOF analysis.

Referring to FIG. 10, in all calculations for velocity and angle distributions we assumed that maximum spreads are approximately twice wider than full width at half maximum Max = 2FWHM. In scheme 101, annotating angle between initial ion direction and recoil direction as β, the probability (solid angle) at isotropic recoil or CID scattering is proportional to Abs[sin(β)]. Assuming a simplest model of $\cos^2(V/V_{max} * \pi/2)$ distribution of recoil velocity, the velocity P(V) and angular P(a) probability distributions are then presented in the graph, supporting Max = 2FWHM relation.

Referring to FIG. 10, in all calculations for velocity and angle distributions we assumed that maximum spreads are approximately twice wider than full width at half maximum Max=2FWHM. In scheme 101, annotating angle between initial ion direction and recoil direction as β, the probability (solid angle) at isotropic recoil or CID scattering is proportional to Abs[sin(β)]. Assuming a simplest model of $\cos^2$ (V/Vmax*π/2) distribution of recoil velocity, the velocity P(V) and angular P(a) probability distributions are then presented in the graph, supporting Max=2FWHM relation.

Focusing Past So-EI Source for MS-MS

Ion angular scattering within some finite length of fragmentation cell increases emittance of fragment ion packets (see Table 2). In all cases the fragment recoil is expected to provide the widest angular divergence with FWHM being 100 mrad in fragmentation cell and 15 mrad in TOF2.

If arranging fragmentation for wide ion packets (10 mm), the ion packet emittance barely fits the acceptance of a singly reflecting TOF. For an L=3 m TOF2 analyzer the ion packet will diverge by 45 mm, which induces losses, particularly if using the long life detector of FIG. 7 with a PMT window 8 mm wide. Additionally, refocusing of ion wide packets is very likely to add notable time aberrations.

Here we disclose a generic solution suitable for a so-EI source. Taking into account that the full angular divergence of a primary ion beam is 5 mrad (FWHM=2.5 mrad) at 5 kV and 15 mrad (FWHM=7.5 mrad) at 500 eV, spatial focusing of parent ions into fragmentation cell provides a solution. Assuming preservation of the phase space at spatial focusing (meaning low aberration systems), the beam can be refocused from 10 mm*15 mrad into 2 mm*75 mrad. Then, after scattering in the fragmentation cell, the overall angular divergence (added as squares with 100 mrad of recoil divergence) will be 130 mrad at 2.5 mm diameter (i.e. 300 mm*mrad). After post-acceleration from 100 eV to 5 keV, the overall divergence of fragment ions will experience a 7-fold reduction (as square root of mean energy ratio) to 20 mrad (FWHM), and the emittance of fragment ions will become 40-50 mm*mrad (FWHM). The disclosed focusing of parent ions provides a 3-fold emittance improvement and makes it compatible with the acceptance of MR-TOF analyzers. For singly reflecting TOF MS analyzers with a compact and long life detector, the transmission improves by a factor of nine, if not using spatial focusing of fragments. If using fragment spatial focusing, the spherical aberrations of the lens system rise as a square of the ion packet diameter, and a three-fold emittance reduction is expected to drop spherical time-of-flight aberrations nine-fold.

Referring again to FIG. 10, phase-space diagrams 102 illustrate the advantage of parent focusing into the fragmentation cell. The smaller (dashed) ellipses correspond to parent ions and the larger (white) ellipses corresponds to fragments. The left diagram, corresponding to spatial focusing of parent ions onto a fragmentation cell provides the least emittance (area of ellipse) for fragment ions. In addition to reducing the emittance, spatial focusing helps confining the ion beam into tight apertures of CID cell at nearly full transmission.

Also note that ion losses would be devastating if using standard open EI source, which has a 3-4 times larger spatial emittance in one direction (compared to the so-EI source), meaning at least a 10-fold lower transmission through a limited acceptance of the CID cell and of the TOF analyzer.

Very similar problems exists in the time-energy space, except the problem is aggregated by the energy partitioning effect (i.e. energy of a fragment ion $E_F$ drops proportional to the fragment mass $M_F$: $E_F=E_M*M_F/M$) and by the large energy spread of initial ions. It is imperative to set an intermediate time-focusing plane in fragmentation cell, ideally combined with the time selector (TIS) plane. Then, this plane becomes an intermediate time-focal plane for the TOF2 stage. After post-acceleration from 500 eV to 5000 eV, the energy spread becomes compatible with the energy acceptance of a singly reflecting TOF (25% at R=10K) and of MR-TOF (10% for R=50K).

The biggest challenge for so-EI is in combining both spatial and temporal focusing planes while limiting aberrations of the focusing system. Here, we propose two novel solutions: (a) using a gridless mirror with a built-in lens behind the source; and (b) using a spatial-focusing gridless accelerator, which mimics half of a gridless ion mirror.

Post Source Decay (PSD)

TOF-TOF methods employing post source decay (PSD) has been developed for MALDI sources with singly reflecting TOF analyzers, as described in U.S. Pat. No. 6,300,627 (LIFT by Bruker), incorporated herein by reference. The post-source decay occurs within the first linear TOF leg. Fragments, corresponding to a particular parent ion of interest, are selected by a time-ion selector (TIS) gate, for example, by Bradberry-Nielsen bipolar wire gate (BN gate) located at the first time-focal plane. Preferably, the first TOF leg is arranged at a notably smaller acceleration potential and all the fragments are post-accelerated after TIS for better time-of-flight focusing in the ion mirror. Fragmentation within the free-field region are prone to a so-called energy partitioning effect—energy of fragment ions drops as a ratio of fragment to parent mass $E'=E*m/M$. There are several methods of time-of-flight focusing developed in MALDI-TOF and MALDI-TOF-TOF. In one method, corresponding to MALDI PSD, the mirror potential is stepped down to focus a particular range of fragment masses (fitting into 20-30% energy acceptance of the ion mirror). The method is slow and ineffective. In another method, fragment ions are accelerated past TIS by at least ⅔ of the acceleration voltage to fit within the energy acceptance of an ion mirror for the entire ensemble of fragment ions. The third method corresponds to pulsed bunching (a pulsed acceleration provides time-of-flight focusing for ions occurring at particular plane) of the fragment ensemble to provide time selection.

Electron Impact ionization is known to form metastable ions, and one may assume using PSD TOF-TOF methods. A fragmentation cell can promote parent ion fragmentation past a so-EI source. However, when applying TOF-TOF methods one should account that the so-EI source provides much larger spatial and time-energy emittance (as shown in Table 1).

Figure 11:
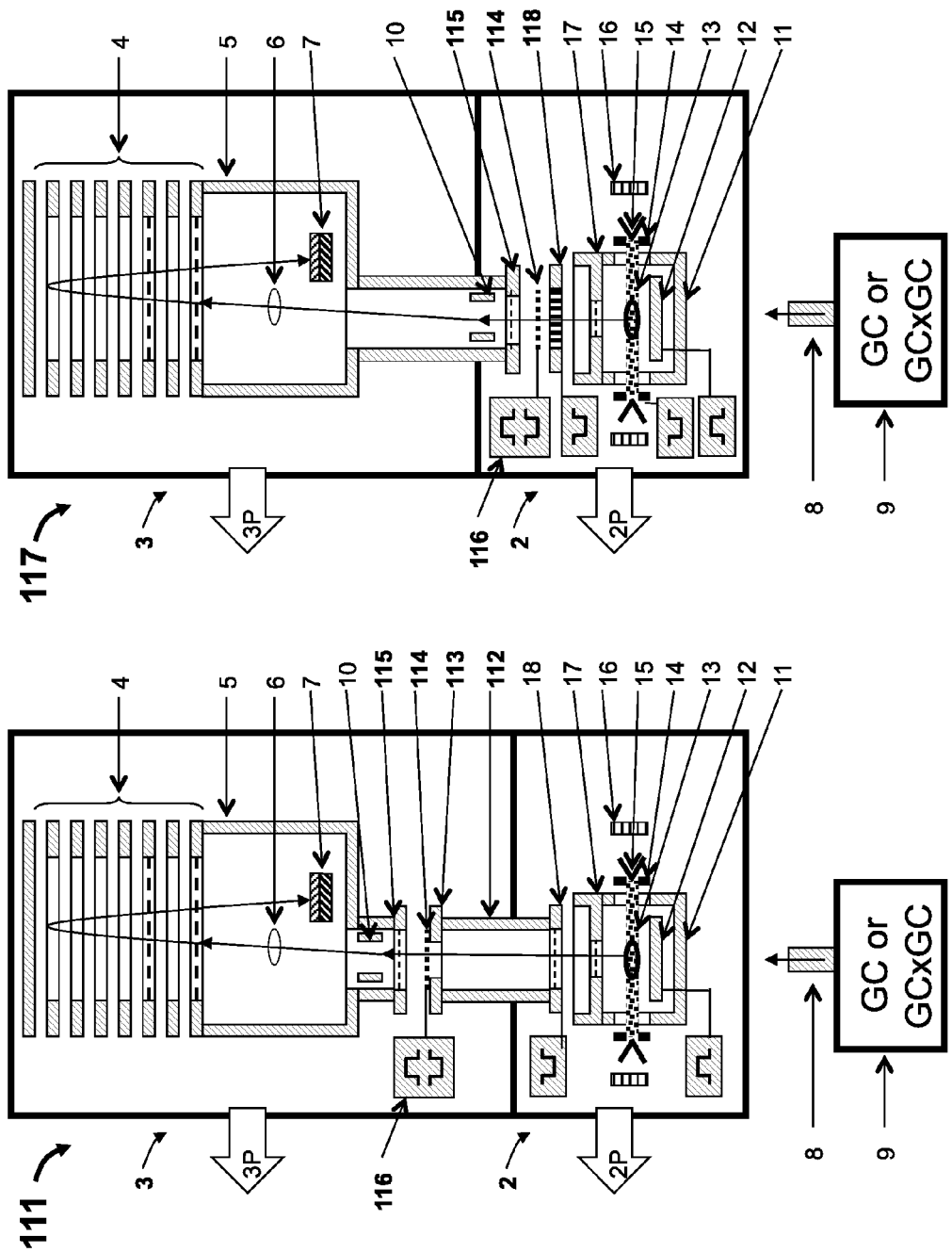
FIG. 11 depicts two embodiments of tandem GC-MS-MS apparatus of the present invention employing post-source decay past the so-EI source and SID fragmentation at gliding angles.

Referring to FIG. 11, an embodiment 111 is presented to illustrate problems of applying conventional TOF-TOF methods with a so-EI source 2. The embodiment 111 employs a grounded so-EI source 2 and a singly reflecting TOF 3. The singly reflecting TOF is shown for simplicity, though an MR-TOF option is also accounted for. The semi-open EI source 2 comprises a source chamber 11 with an extraction electrode 17 having an extraction aperture 27 between 0.1 cm$^2$ and 1 cm$^2$ and having positively biased slits 14. At 1 mL/min helium flow the gas pressure is estimated as 0.1-1 mTor. The apparatus 111 further includes an intermediate drift chamber 112 with a differential aperture in a plate 113 and electrically connected to a pulsed acceleration plate 18 having a slit at an intermediate accelerating voltage between −300V and −1000V, which is preferably pulsed. The apparatus 111 also includes a time-selector gate 114 connected to a pulse generator 116 and a TOF entrance mesh 115 connected to the acceleration voltage of drift chamber 5 (typically −5 kV).

In operation, limited amount of metastable decay occurs past the so-EI source 2. The gas pressure in the source chamber 11 is elevated compared to standard open EI sources, which promotes collisional induced dissociation (CID). At an optimal 0.5 cm$^2$ source opening (extraction aperture 27) in the extraction electrode 17 and a 1 mL/min helium flow past GC, we calculate gas pressure in the source is approximately 1E-6 Bar, corresponding to a mean free path of 3 cm for 500 amu ions with an 100 A$^2$ (1E-14 cm$^2$) cross section. Both effects are expected to cause metastable fragmentation in the intermediate drift chamber 112. The differential aperture in plate 113 may be used for to provide for approximately a single ion collision with helium molecules. As a numerical example, the gas pressure in the intermediate drift chamber 112 is 0.3 mBar and the length of the intermediate drift chamber 112 is 10 cm. After fragmentation, fragments fly within the field free region of the intermediate drift chamber 112 with the velocity of parent ions set by TIS (time selector gate 114), by, for example, switching off scattering deflection for a short period of time.

Problems and Solutions for PSD-TOF-TOF Method

Specifics of the so-EI source (wide beam, large energy spread, and short distance to first time focus) make prior art TOF-TOF methods a poor solution.

First problem is the large time spread of parent ions if arranging time-focal plane far from the so-EI source. To arrange for a 5 cm time-focal distance (required for any reasonable time selection of parent ions), the field strength in the so-EI source has to be dropped more than 25 times (4 Volts/mm). As an estimate, the focal length of two-stage acceleration (at a negligibly short second acceleration stage) $L_T=2$ an, where a is the length of the first stage and n is the ratio of velocities past stages. At $L_T=50$ mm and a=5 mm, one needs to set n to 5 (i.e. the acceleration field strength is 4 V/mm), which increases turnaround time to unreasonably large value of 150 ns for 500 amu. Notably for linear TOF MALDI this problem is much softer at a small relative energy spread in continuous mode or when using delayed extraction as described in U.S. Pat. No. 5,760,393 (which is incorporated herein by reference).

To extend the focal distance and to reduce the turnaround time, the source may be operated with delayed extraction. Slit potential is pulse-adjusted to temporally lock the electron beam and the ion extraction pulse is applied at a microsecond delay. However, the effect is limited as was experimentally discovered in our own experiments. For this reason, here we disclose the use of a reflecting mirror behind the so-EI source (as describe hereinafter and illustrated in FIG. 12) in order to accommodate the time-focal plane at a practical distance from the source. As a numerical example, the focal length is adjusted to $L_T=10$ mm in order to keep the acceleration field at 100 V/mm. The time-selector is then moved into the next focal plane, which could be moved much further from the source to provide sufficient resolution of time gate in the order of 50 to 100.

A co-pending application, incorporated herein by reference, by the present inventors describes an alternative solution, wherein the focal plane is moved much further away from the source by using an additional buncher.

A second problem arises due to a large width (7 mm) of ion packets past the so-EI source. Fragment recoil forms an angular spread of 30 mrad (Max) at the TOF2 stage (Table 2); thus, the overall packet emittance becomes too high (200 mm*mrad) even for singly reflecting TOF analyzers. If no spatial focusing is applied, ion packets would spread for 30-60 mm in a 3 m flight path of the TOF analyzer. The problem of beam focusing onto the detector may be partially solved by increasing acceleration potential to approximately 20 keV (MALDI case), which is not desirable for a low cost GC-MS instrument. This problem also can be solved by using a lens system, which, however, adds a notable time spread when focusing wide and diverging ion packets with a large emittance.

In order to reduce the overall emittance of fragment ions and to handle spatial focusing at a minimal time spread, we disclose spatial focusing of parent ions prior to fragmentation into a small size beam of approximately 2 mm size. Then, emittance of fragment ions drops 60 mm*mrad (compared to 200 mm*mrad without the disclosed focusing). To reduce spherical aberrations at the step of parent ion focusing, here we disclose either: (a) using a backstage ion mirror with a built-in lens that compensates for spherical aberrations; or (b) using a so-EI acceleration stage having spatial focusing within the accelerator which resembles half of the ion trajectory and fields of method (a). The reflecting ion mirror is preferable since it allows setting an intermediate time focusing close to the source and, thus, using normal acceleration fields (100-200 V/mm) to reduce turnaround time to 7 ns at 500 amu.

A third problem arises due to a combination of: (a) the wide energy spread for parent ion packets past the so-EI source (previously described as being estimated at 100-150 eV); and (b) the prolonged decay path in the PSD method. Metastable decay adds 20% velocity spread (see Table 2). At a 10 cm flight path in the first TOF leg (TOF1), the fragment will separate from the parent ion by +/−1 cm and 30-700 ns flight time, which will create a large product of the time and energy spreads ΔT*ΔK and would, thus, ruin resolution at the TOF2 stage. Because of large the energy spread in the parent ion packet, pulsed post-acceleration (bunching, widely used in MALDI-TOF-TOF) would become ineffective. To make MS-MS effective, the fragmentation has to be arranged at a much shorter distance and near to the time-focal plane. Here we propose setting a short (5-10 mm) CID cell at an elevated gas pressure to reduce the fragmentation path. To induce a single collision (on average) the cell gas pressure is adjusted to 3-6 mTor. The cell opening should be at least of a 2-3 mm size to pass through the ion beam, earlier estimated to be focused onto 2 mm size. To avoid excessive gas loads, we disclose mounting the CID cell in the first pumping stage together with the so-EI source. In embodiments with the back mirror, the so-EI source itself may be operated as a CID cell. Alternatively, we disclose using a pass-through SID cell operating at gliding collisions. For the same reason of improving time-energy emittance of fragment ions we disclose using a short length (3-5 mm) of the SID cell.

Thus, specifics of the so-EI source (wide beam, large energy spread, and short distance to first time focus) require additional solutions for spatial and time focusing, so as arranging short fragmentation cells.

Embodiment with SID Cell

Again referring to FIG. 11, the improved MS-MS apparatus 117 includes the previously described so-EI source 2 and TOF analyzer 3, a short (3-5 mm) SID cell 118, and a TIS gate 114 driven by pulse generators 116. Preferably (though not necessarily), an additional pulse generator is connected to at least one of the slits 14. The SID cell 118 is formed with parallel channels (which may be, for example, 0.5-1 mm wide and 3-5 mm long). Preferably the channels are tilted from the TOF axis at an angle of approximately 5-10-degrees, but could vary from this range. The geometry of the channels is set to provide 30-50% through transmission. The SID cell 118 is placed in close vicinity (20-30 mm) of the extraction aperture 27 in plate 17. Preferably, the SID cell 118 is removable for switching between MS-only and MS-MS regimes. And, preferably, to reduce charge transfer at SID fragmentation, the SID cell 118 is coated with a vacuum grease, such as with long fluoro-polymers having a vapor pressure in the 1E-7 Tor range or below.

In one operation mode, the electron beam is shut by applying a negative pulse to slits 14 of approximately 5-10 μs prior to applying an ejecting pulse to repeller electrode 12. During the delay, an ion cloud with thermal velocities of 0.14 mm/μs for 500 amu ions at 50 meV energy (determined in experimental studies of the so-EI source) will expand from 1-1.5 mm to 4-5 mm. Then, the velocities become strongly correlated with the ion position, and the extraction pulse amplitude could be reduced to 20-30 V/mm (for example, using 200-300V pulse amplitude at 10 mm acceleration gap), while still maintaining a 7 ns non-correlated turnaround time for 500 amu ions. Ions are accelerated to approximately 500 eV between the extraction aperture 27 the plate 17 and SID cell 118, assumed to be sufficient to induce SID fragmentation at gliding 5-10 degree collisions with channel surface. The surface induced dissociation at gliding collisions is expected to introduce radial and axial energy spreads—both within 1 eV. Fragments are expected to move with approximately the same velocity (within +/−10% of parent ion velocity). The TIS gate 114 (which may, for example, comprise a BN gate, which has already been described) is set in close vicinity of the SID cell 118 to minimize ion packet spread in the time-energy space. Fragment ions are accelerated to 5 kV energy past the TIS gate 114 to fit an energy acceptance of the TOF analyzer 3. Optionally, fragments are pulse-accelerated past the SID cell 118 for time focusing onto TOF detector 7 (for example, by utilizing a bunching method).

The MS-MS apparatus 117 provides several improvements over the embodiment 111. First, it extends the focal plane distance 2-fold-3-fold (i.e. by 20-30 mm). Second, it matches the focal plane with the fragmentation region. Third, it reduces the time spread at fragmentation due to using a short cell. Fourth, it reduces spread in the time-energy space due to time focusing onto the fragmentation cell. Because of fragments recoil, the maximum of relative velocity spread is +/−10% and FWHM is 10%. The beam at a 14 mm/μs velocity passes 3 mm SID cell 118 within 200 ns and the 20% velocity variation introduces a 40 ns time spread (FWHM), which, though notable, is still much less compared to 700 ns spread at the intermediate drift chamber 112 of embodiment 111. However, the MS-MS apparatus 117 is far from being optimal. It does not employ spatial focusing of the primary ion beam (due to too short of a distance to the SID cell 118 for spatial focusing) and, thus, it forms large spatial emittance of fragment ions. The angular spread of fragment ions is estimated as 200 mrad within CID cell and 30 mrad in TOF2 leg after post-acceleration. Assuming a full width (10 mm) of ion packets, the spatial emittance is 300 mm*mrad in the TOF2 leg (within TOF analyzer 3), which is still large even for singly reflecting TOF and significantly above the acceptance of MR-TOF analyzers (40-50 mm*mrad). Besides, close vicinity of the SID surface to hot ion source introduces an additional danger of source contamination. Solutions to those problems are disclosed in following-described embodiments.

Preferred MS-MS Embodiment

Figure 12:
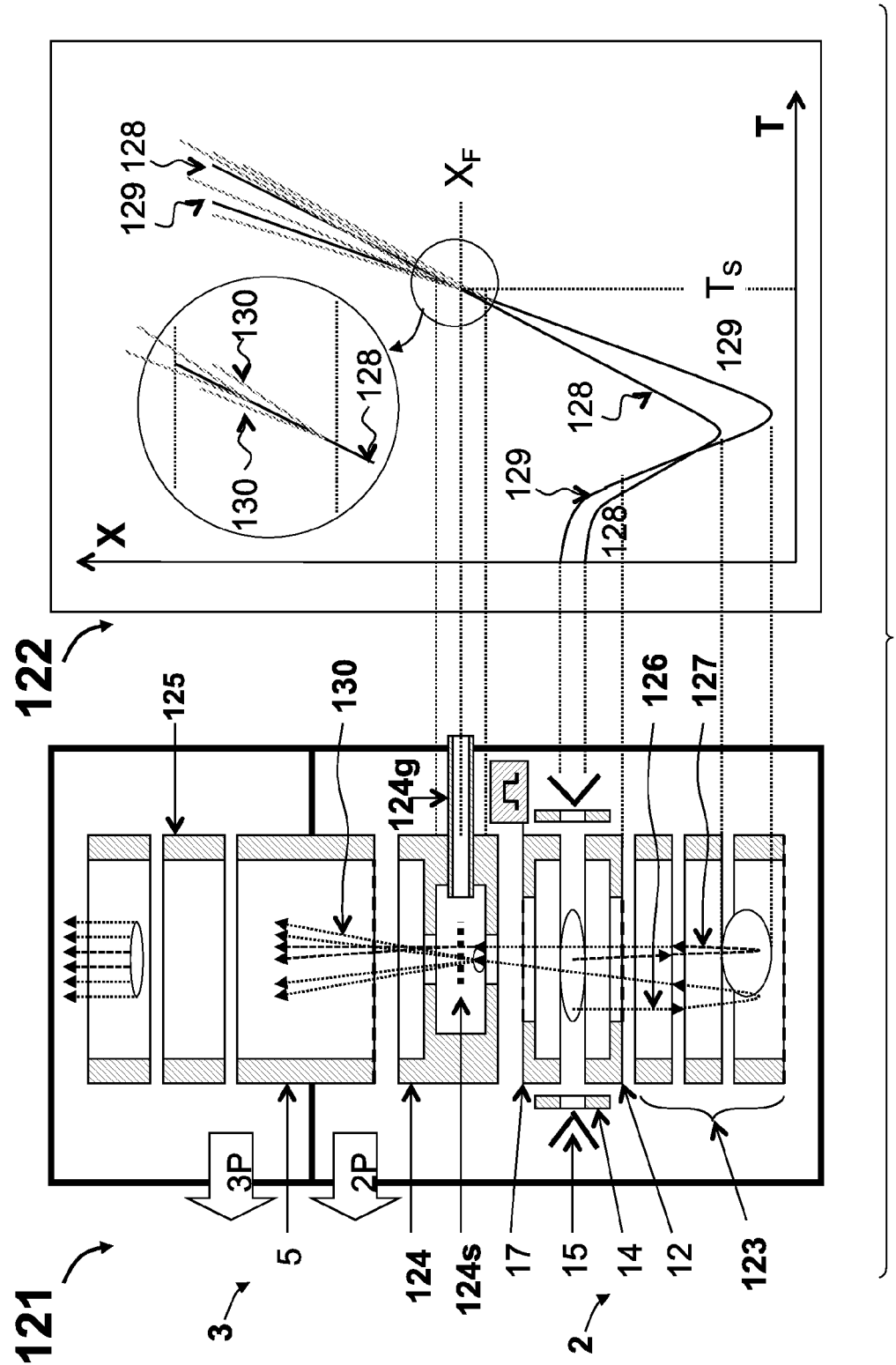
FIG. 12 depicts an embodiment of tandem TOF apparatus of the present invention, with spatial ion refocusing in the ion mirror located behind the so-EI source, together with time diagrams illustrating simultaneous time-of-flight focusing.

Referring to FIG. 12, one preferred embodiment of the tandem MS apparatus 121 of the present disclosure includes a semi-open (so-EI) source 2, a time-of-flight mass spectrometer 3, a fragmentation cell 124, shown in FIG. 12 as a CID cell, and a gridless spatially focusing ion mirror 123. The ionization volume of the so-EI source 2 (i.e. the space between plates 12 and 17) has a total opening between 0.1 cm$^2$ and 1 cm$^2$ for the concentration of analyte molecules and has positively biased slits 14 for retaining ions and removing secondary electrons. The shown CID cell 124 has a helium line supply 124g and time-ion selector TIS bipolar mesh 124s. The cell preferably has 2-3 mm openings, a 5-10 mm length, and is filled with helium to approximately 3-6 mTor gas pressure to arrange one ion to gas collision on average. The cell is located within the first differentially pumped stage evacuated by pump 2P. The gas load from CID cell appears comparable to the gas flow from a gas chromatograph (1 mL/min). The TOF MS 3 may be either singly reflecting TOF or multi-reflecting TOF. The drift region 5 of the TOF MS 3 comprises a lens located approximately 50-100 mm past the CID cell 124. Preferably, the exit of CID cell 124 and entrance of the drift region 5 have the form a weak focusing accelerating lens.

In operation, after accumulating ions in the source 2, a push out pulse (say 1000V amplitude at 10 mm ionization gap) is applied to the top plate 17, which forces ions to fly into the mirror 123 at a mean K=500 eV energy and at approximately ΔK=100 eV energy spread. The gridless ion mirror 123 is designed for X|X=0 spatial focusing and T|K=0 time per energy focusing in the focal plane, coinciding with the center of fragmentation cell 124 and bipolar mesh 124s. The spatial focusing is illustrated by ion trajectories in physical space and the time-energy focusing by diagram 122 with distance-time axes. Trajectory 126 with large initial X and a zero initial angle is focused into the center of the CID cell 124 (X|X=0). The trajectory 127 corresponds to zero initial X and a moderate initial angle a (which was previously assessed in this disclosure as 2a=15 mrad at 500 eV). Since the ion source 2 is close to CID cell 124, the initially diverging trajectories will be converted into a parallel beam, because of X|X=0 due to principle of reverse trajectories (parallel-to-point also means point-to-parallel in the reversed trajectory). The beam size for trajectories 127 may be estimated as 15 mrad*100 mm=1.5 mm assuming 100 mm source-to-mirror cap entrance. Trajectories 126 can be focused into a very tight beam but at 50 mrad full divergence, which was shown to be comparable to a full divergence gained in the CID cell 124. Contrary to a conventional lens, the ion mirror with a built-in lens is capable of removing spherical aberrations (i.e. T|xx=0 at T|x=0). The mirror also compensates multiple other aberrations, such as T|k=0 and T|kk=0, T|a=0.

Time-of-flight focusing is illustrated by X-T diagram 122. Curves 128 and 129 correspond to ions starting at an extreme X-distance from the electron beam center. As a result, they gain different amounts of energy. Intersections of curves 128 and 129 correspond to temporal focusing (i.e. T|k=0). The first time-focal plane occurs past the source and the second occurs in the center of the CID cell 124. The dashed lines indicate the coordinate X-correspondence between X-T graph 122 and a location in the apparatus 121. The insert in the graph zooms-in around the X of the CID cell 124. Though initial trajectories 128 and 129 intersect, the newly born fragments will have slightly different velocities shown by curves 130. Those curves 130 will originate from initial curves 128 and 129. However, though there appears some diffusion in T-K correlation, the non-correlated time spread may be reduced by using a short CID cell 124 (5-10 mm). Accounting for +/−10% difference in fragment velocities, the non-correlated time spread can be assessed as 20% of time spent in the CID cell 124 and is assessed as 20 ns. Thus, with the accuracy of 20 ns, the CID cell 124 becomes the effective emitter with a minimal time spread and a large energy spread, which is known to be time-focused by singly reflecting TOF or MR-TOF MS. Optionally, a bunching pulse is applied to the CID cell 124 for compressing ion packets on the TOF detector. As we described earlier, a carefully designed acceleration stage may provide spatial focusing with minimal spherical aberrations.

Figure 13:
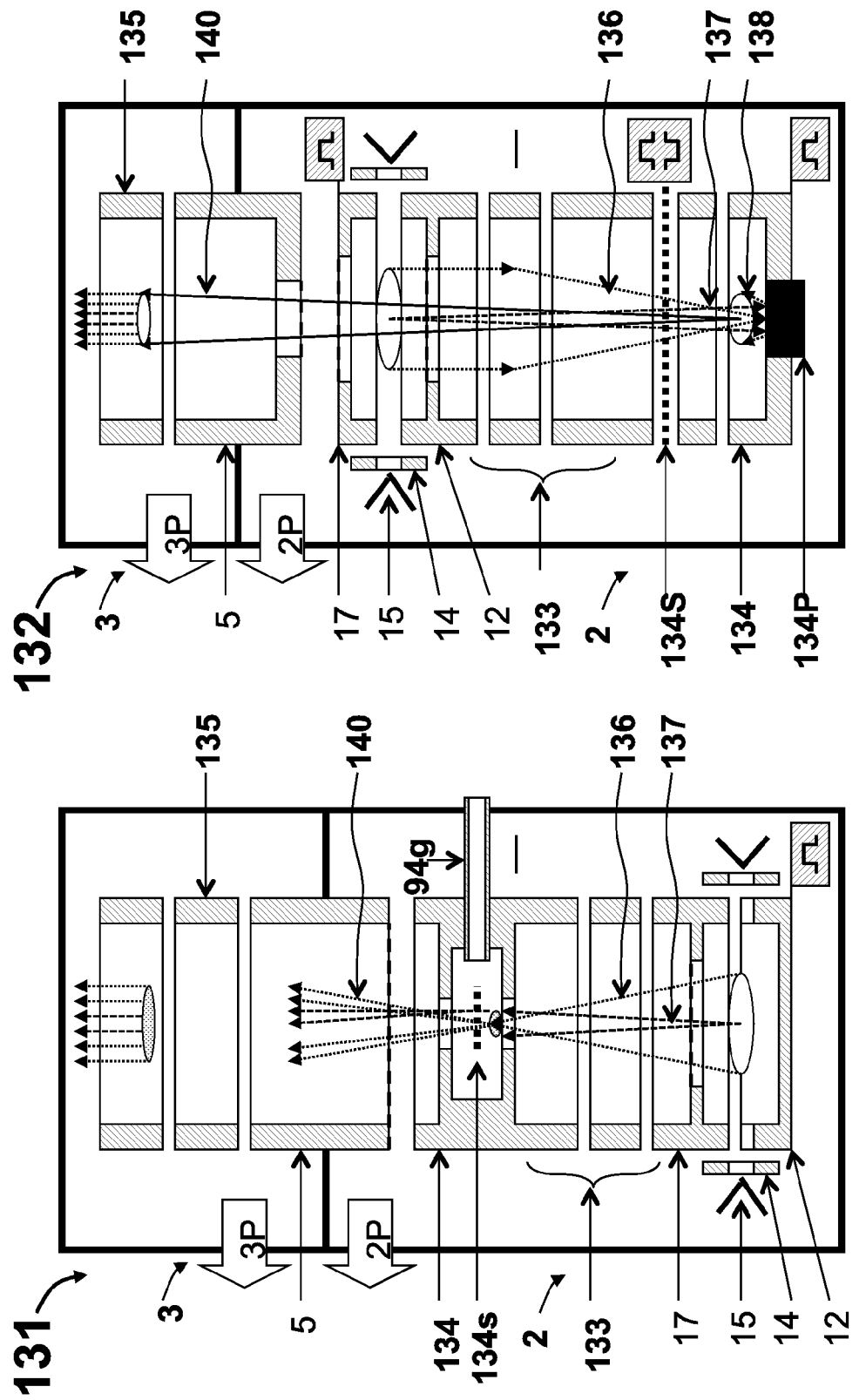
FIG. 13 depicts two MS-MS embodiments with spatial and time focusing arranged with elements located behind the so-EI source; in embodiment 131 the focusing is arranged by curved fields in the so-EI source; in embodiment 132—by curved fields in the SID fragmentation cell.

Referring to FIG. 13, another preferred tandem MS 131 embodiment of the present disclosure includes a semi-open source 2, a time-of-flight mass analyzer 3, a fragmentation cell 134, and a spatially focusing lens 133. Plates 12 and 17, which form an accelerator, are designed to provide the spatially focusing lens, mimicking half of the ion mirror. The tandem MS 131 differs from very similar apparatus 121 only by using different spatially focusing means—apparatus 121 utilizes a mirror with built in-lens 123 and tandem MS 131 utilizes an accelerator with built in lens 133.

Again referring to FIG. 13, another tandem MS 132 embodiment of the present disclosure includes a semi-open source 2, a time-of-flight mass analyzer 3, a lens 133, a surface induced dissociation cell 134 with a probe 134P coated by fluoropolymer, and time selective gate 134s.

In operation, a push-out pulse is applied to plate 17 for sending ion packets towards the SID cell 134. The time selective gate 134s selects ion packets with a bipolar wire gate, which is open for short time while admitting parent ions and then later for passing a moderate band of fragment ions. The time selective gate 134s is located as close to the SID cell 134 surface as possible. The parent selection is based on changing axial energy as described in WO2013192161, which is incorporated herein by reference. At a strong deceleration, the deficiency of axial energy causes ions to be reflected, or at least strongly diverted. After an approximate 1-2 μs delay after parent ions hit the surface and form slow fragment ions, an accelerating pulse is applied to electrode SID cell 134 and probe 134P, emitting fragment ions. The tandem MS 131 has a very limited capability of mass selection to satisfy both the selection of parent and the transmission fragment ions. In one practical example, the gate can serve for low mass cut off, which is still quite useful for extracting MS-MS spectra at presence of strong hydrocarbon matrix, primarily forming low mass ions.

The WO2013192161 application by present inventors, incorporated herein by reference, describes multiple advanced schemes with SID fragmentation arranged within an MR-TOF analyzer. Here we disclose that all those MR-TOF-SID-MR-TOF schemes would be strongly benefited by using a so-EI source instead of a standard open source, when using a spatial focusing scheme of a primary ion beam as shown in FIGS. 12-13.

Figure 14:
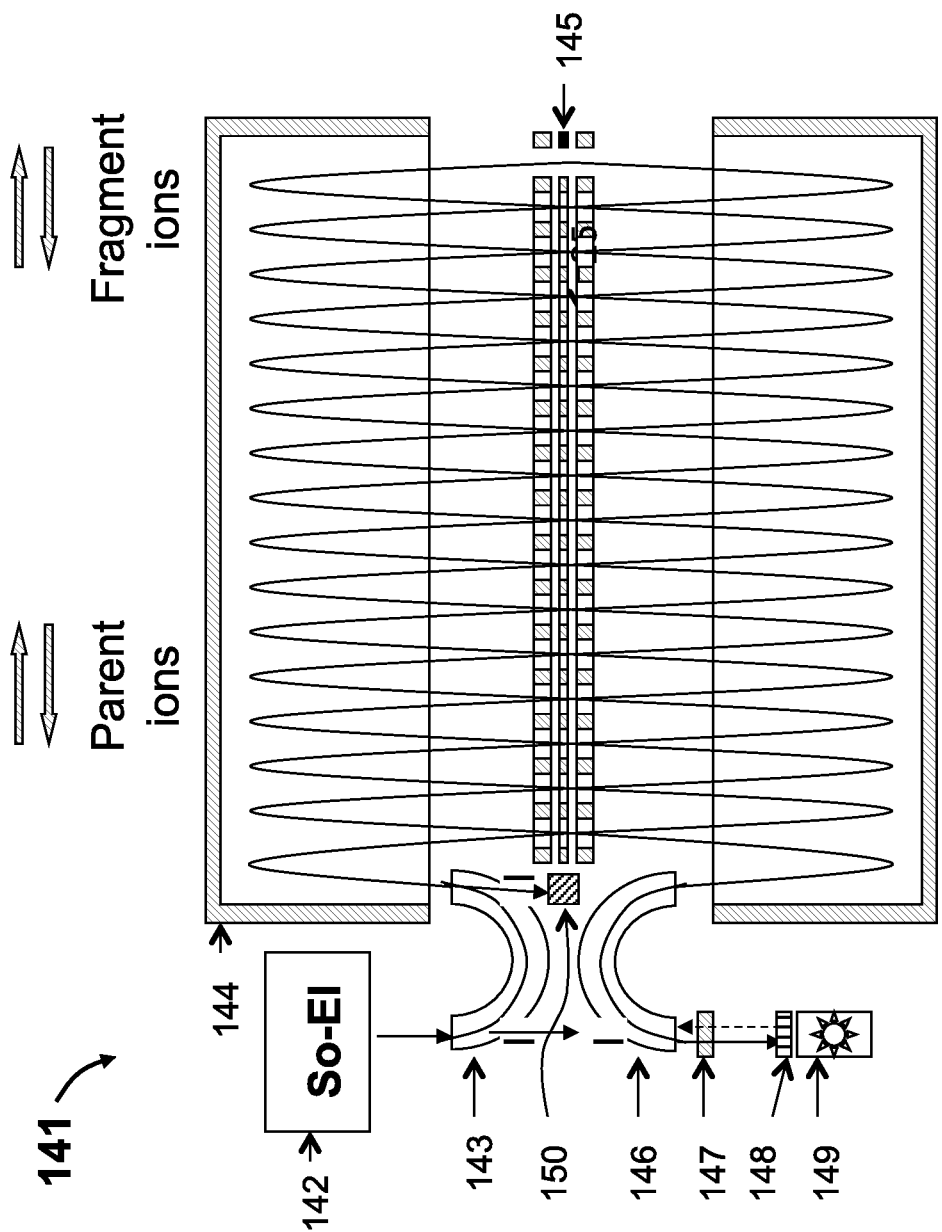
FIG. 14 depicts an embodiment of tandem TOF apparatus, using SID cell incorporated behind the so-EI source with SID surface aligned with time-fronts of ion packets.

Referring to FIG. 14, an embodiment 141 of the disclosure comprises a MR-TOF tandem with external so-EI source 142 and external SID cell 149 coupled to a MR-TOF analyzer 144 via curved isochronous inlets 143 and 146. WO2013192161 is herein incorporated by reference.

In operation, in addition to non-redundant sampling on a TIS gate 147 and to time-encoded delay of SID pulsing, here we disclose another dimension of encoding—encoding by frequent pulsing of the external so-EI source 142. Higher dimension encoding adds a higher degree of non-redundancy and allows yet a higher duty cycle of the tandem.

Use of the external so-EI source 142 highly increases brightness of the ion source compared to open sources. The new schemes of spatial refocusing disclosed in this disclosure (see, for example FIGS. 12-13) further improve compatibility of MR-TOF analyzer with the so-EI source.

Figure 15:
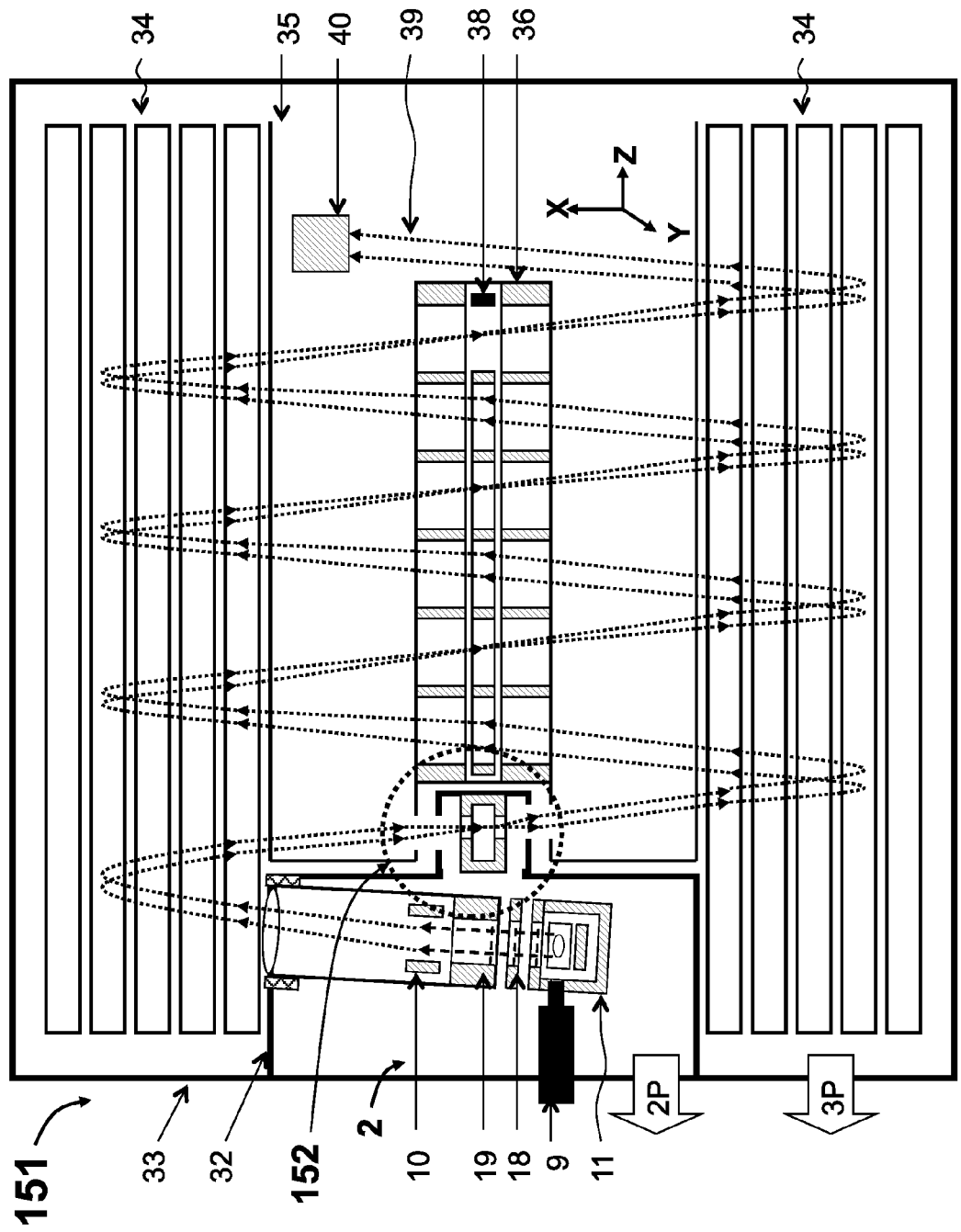
FIG. 15 depicts embodiment of tandem TOF apparatus with a CID cell incorporated into the MR-TOF analyzer and evacuated through the ion source differential pumping stage.

Referring to FIG. 15, an embodiment 151 of tandem MS includes a so-EI source 2 built into an MR-TOF analyzer 33 and a fragmentation cell 152. The so-EI source 2 is surrounded by differential pumping wall and is evacuated by pump 2P. The source is tilted as described previously and illustrated in FIG. 3. The difference of embodiment 151 from apparatus 3 is in the use of fragmentation cell 152. To reduce gas load, a shroud surrounding the CID cell 152 is connected to the first differentially pumped stage 2P. The ion optical scheme of the shroud and of the CID cell 152 is optimized for improved ion transmission. The entrance part provides local spatial focusing onto the cell center and the exit part provides conversion of divergent packets into a nearly parallel beam.

In addition to described exemplary MS-MS systems, other TOF-TOF tandems may be constructed based on the so-EI-MR-TOF combination system disclosed herein. Such systems usually include several elements of the following group: (i) a timed ion selector for selecting parent ions beyond the ion source; (ii) a gridless ion mirror behind the so-EI source 2 for simultaneous temporal and spatial focusing of primary ions into a fragmentation cell; (iii) a curved-field accelerator built into the so-EI source 2 for simultaneous temporal and spatial focusing of primary ions into a fragmentation cell; (iv) a surface induced dissociation SID cell facing primary ion packets; (v) a surface induced dissociation SID arranged at gliding angle relative to trajectory of parent ion packets; (vi) a collisional induced dissociation CID within a short CID cell with a length L under 1 cm at gas pressure P adjusted to maintain a product P*L between 1 cm*mTor and 5 cm*mTor, which corresponds to a single average collision of parent ions; (vii) a collisional-induced dissociation CID cell arranged within the source 2 by choosing a source opening between 0.1 cm$^2$ and 0.3 cm$^2$; (viii) pulsed accelerator beyond a fragmentation cell; (ix) a spatial focusing lens beyond a fragmentation cell; (x) a post-acceleration of fragment ion packets beyond a fragmentation cell; (xi) a steering means beyond a fragmentation cell.

While this specification contains many specifics, these should not be construed as limitations on the scope of the disclosure or of what may be claimed, but rather as descriptions of features specific to particular implementations of the disclosure. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multi-tasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

A number of implementations have been described. Nevertheless, it will be understood that various modifications may be made without departing from the spirit and scope of the disclosure. Accordingly, other implementations are within the scope of the following claims. For example, the actions recited in the claims can be performed in a different order and still achieve desirable results.

What is claimed is:

1. A chromato-mass spectrometer comprising:
   a single or dual stage gas chromatograph;
   a semi-open EI source defining a source opening having an area between about (0.1 to 1) square cm and positively biased slits for an electron beam configured to form an electrostatic well for accumulating ions, wherein the semi-open EI source is arranged in a separate differential pumping stage and provides pulsed ejection of accumulated ions;
   a multi-reflecting time-of-flight analyzer having a periodic lens and a time-of-flight detector; and
   an interface comprising a set of focusing and deflecting ion-optical elements coupling said semi-open EI source with said analyzer in such a way that a spatial emittance of said semi-open EI source is matched to an acceptance of said analyzer and that time broadening of ion signal due to said spatial emittance is eliminated at said time-of-flight detector at least to a first order of Tailor expansion.

2. A mass spectrometer as in claim 1, to increases dynamic range by frequent encoding pulsing, further comprising: (i) a synchronizing clock capable of triggering at programmed non-uniform time intervals with time increments no more than 10 ns; (ii) a pulse generator capable of pulsing at average frequency at least 30 kHz; and (iii) a data system for spectral decoding.

3. A mass spectrometer as in claim 1, wherein said interface is selected from the group consisting of: (i) a differentially pumped chamber, accommodating said semi-open EI source and placed between said ion mirrors; (ii) an isochronous set of curved electrostatic sectors for external mounting of said source; (iii) an isochronous set of curved electrostatic sectors for displacing ion trajectory; (iv) an energy filter composed either of electrostatic sectors or deflectors combined with spatially focusing lens; (v) a lens-deflector with pulsed power supply for deflecting helium ions or for crude mass selection; (vi) a gridless ion mirror placed behind said semi-open EI source; (vii) a curved field accelerator built into said source for isochronous spatial focusing; (viii) a differential aperture placed at a plane of spatial focusing and followed by spatially focusing lens; (ix) a telescopic lens system for reducing spatial packet size at the expense of widening angular spread; and (x) a combination thereof.

4. A mass spectrometer as in claim 1, wherein parameters of said multi-reflecting time-of-flight analyzer are selected from the group consisting of: (i) a cap to-cap distance between 0.5 m and 1.5 m; (ii) a periodic lens with lens pitch between 5 mm and 20 mm; (iii) an ion flight path between 7 and 30 m; (iv) an acceleration voltage between 3 keV and 10 keV; and (v) a combination thereof.

5. A mass spectrometer as in claim 1, wherein said multi-reflecting time-of-flight analyzer is of either planar or cylindrical symmetry.

6. A mass spectrometer as in claim 1, further comprising an ion transferring optics for introducing external ions into said so-EI source and one source selected from the group consisting of: (i) a chemical ionization source; (ii) a photo chemical ionization source; and (iii) an ion source with conditioned plasma.

7. A mass spectrometer as in claim 1, further comprising an inlet for external delivery of analyte molecules from one source selected from the group consisting of (i) a molecular beam generator; (ii) a molecular separator for splitting helium and analyte flows; and (iii) a combination thereof.

8. A mass spectrometer as in claim 1, wherein said detector comprises a magnetic ion to electron converter, a scintillator covered by conductive mesh, and photo-electron multiplier with extended life time.

9. A mass spectrometer as in claim 1, to provide MS-MS capabilities, further comprising at least one means selected from the group consisting of: (i) a timed ion selector for selecting parent ions past said ion source; (ii) a gridless ion mirror behind said so-EI source for simultaneous temporal and spatial focusing of primary ions into a fragmentation cell; (iii) a curved-field accelerator built into said so-EI source for simultaneous temporal and spatial focusing of primary ions into a fragmentation cell; (iv) a surface induced dissociation SID cell facing primary ion packets; (v) a surface induced dissociation SID arranged at gliding angle relative to trajectory of parent ion packets; (vi) a collisional induced dissociation CID within a short CID cell with length L under 1 cm at gas pressure P adjusted for P*L product between 1 and 5 cm*mTor corresponding to single average collision of parent ions; (vii) a collisional induced dissociation CID cell arranged within said source by choosing said source opening between 0.1 and 0.3 $cm^2$; (viii) pulsed accelerator past a fragmentation cell; (ix) spatial focusing lens past a fragmentation cell; and (x) post-acceleration of fragment ion packets past a fragmentation cell; (xi) steering means past a fragmentation cell; and (xii) a combination thereof.

10. A mass spectrometer as in claim 1, further comprising a pulse generator past said source for a purpose selected from the group consisting of: (i) adjusting time focal plane of ion packets, pulse ejected from said source; (ii) adjusting energy or energy spread of ion packets, pulse ejected from said source; and (iii) converting a continuous flow past said source into ion packets, followed by energy filtering of said ion packets.

* * * * *